(12) United States Patent
Tsuchiya

(10) Patent No.: US 9,097,643 B2
(45) Date of Patent: Aug. 4, 2015

(54) IMAGING CONTROL APPARATUS, RADIOGRAPHIC IMAGING SYSTEM, AND IMAGING CONTROL METHOD

(71) Applicant: CANON KABUSHIKI KAISHA, Tokyo (JP)

(72) Inventor: Keiji Tsuchiya, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 329 days.

(21) Appl. No.: 13/727,295

(22) Filed: Dec. 26, 2012

(65) Prior Publication Data

US 2013/0170617 A1 Jul. 4, 2013

(30) Foreign Application Priority Data

Dec. 28, 2011 (JP) ................................. 2011-288682

(51) Int. Cl.
| | |
|---|---|
| H01L 31/08 | (2006.01) |
| G01N 23/04 | (2006.01) |
| H01L 27/00 | (2006.01) |
| A61B 6/00 | (2006.01) |

(52) U.S. Cl.
CPC .............. *G01N 23/04* (2013.01); *A61B 6/4233* (2013.01); *A61B 6/54* (2013.01)

(58) Field of Classification Search
CPC .. H01L 31/08; H01L 27/14658; G01N 23/04; G01N 23/046
See application file for complete search history.

(56) References Cited

U.S. PATENT DOCUMENTS

| | | | | |
|---|---|---|---|---|
| 5,029,016 | A * | 7/1991 | Hiyama et al. | 358/403 |
| 5,986,278 | A * | 11/1999 | Becker et al. | 250/580 |
| 7,599,541 | B2 * | 10/2009 | Hayashida | 382/132 |
| 7,860,285 | B2 * | 12/2010 | Kariathungal et al. | 382/128 |
| 8,831,324 | B2 * | 9/2014 | Penenberg | 382/131 |
| 8,989,474 | B2 * | 3/2015 | Kido et al. | 382/132 |
| 2005/0088566 | A1 * | 4/2005 | Tamura et al. | 348/362 |
| 2006/0023839 | A1 * | 2/2006 | Shoji | 378/97 |
| 2009/0168966 | A1 * | 7/2009 | Suzuki et al. | 378/116 |
| 2010/0019176 | A1 * | 1/2010 | Tanabe | 250/591 |
| 2010/0104167 | A1 * | 4/2010 | Sakaguchi et al. | 382/132 |
| 2010/0111257 | A1 * | 5/2010 | Takekoshi | 378/91 |
| 2011/0044430 | A1 * | 2/2011 | Takenaka et al. | 378/98.7 |
| 2011/0164724 | A1 * | 7/2011 | Ohta et al. | 378/62 |
| 2012/0063570 | A1 * | 3/2012 | Furuichi et al. | 378/98.2 |
| 2012/0105655 | A1 * | 5/2012 | Ishii et al. | 348/208.4 |
| 2012/0128126 | A1 * | 5/2012 | Ishii | 378/62 |

(Continued)

FOREIGN PATENT DOCUMENTS

| | | |
|---|---|---|
| JP | 3-62500 A | 3/1991 |
| JP | 2000-292598 A | 10/2000 |

(Continued)

*Primary Examiner* — David A Vanore
(74) *Attorney, Agent, or Firm* — Canon USA Inc. IP Divison

(57) ABSTRACT

A radiographic imaging apparatus includes: a radiation detection array configured to store charges to acquire an image signal; an output unit configured to output radiation image data based on the image signal to an external apparatus; a detection unit configured to detect an imaging mode changeover instruction; and a control unit configured to, when the detection unit detects an imaging mode changeover instruction during one unit of imaging processing including the charge storage and the charge-based radiation image data output to an external apparatus, control whether the imaging processing is to be interrupted, based on an operating state of the radiographic imaging apparatus.

9 Claims, 23 Drawing Sheets

(56) References Cited

U.S. PATENT DOCUMENTS

| | | | |
|---|---|---|---|
| 2012/0224670 A1* | 9/2012 | Kiyohara et al. | 378/62 |
| 2013/0001429 A1* | 1/2013 | Dowaki et al. | 250/394 |
| 2013/0168558 A1* | 7/2013 | Tsuchiya | 250/363.01 |
| 2013/0170617 A1* | 7/2013 | Tsuchiya | 378/62 |
| 2014/0211922 A1* | 7/2014 | Kuwabara et al. | 378/97 |
| 2014/0239188 A1* | 8/2014 | Tezuka | 250/394 |

FOREIGN PATENT DOCUMENTS

| | | |
|---|---|---|
| JP | 2003-33340 A | 2/2003 |
| JP | 2009-272673 A | 11/2009 |

\* cited by examiner

FIG.4

| Tx OF X-RAY GENERATION UNIT = 400 ± 30ms ||
|---|---|
| FRAME RATE Fr | DECIMAL NUMBER a |
| 30 | 0.8 |
| 20 | 0.8 |
| 15 | 0.8 |
| 10 | 0.8 |
| 5 | 0.5 |
| 2 | -0.5 |

FIG.7

| TIME Ts TILL X-RAY RADIATION FOR GENERAL IMAGING = 300 ms | | |
|---|---|---|
| FRAME RATE Fr | TIME Tf5max (ms) | TIME Tc (ms) |
| 30 | 100 | 400 |
| 20 | 100 | 400 |
| 15 | 100 | 400 |
| 10 | 100 | 400 |
| 5 | 200 | 500 |
| 2 | 500 | 800 |

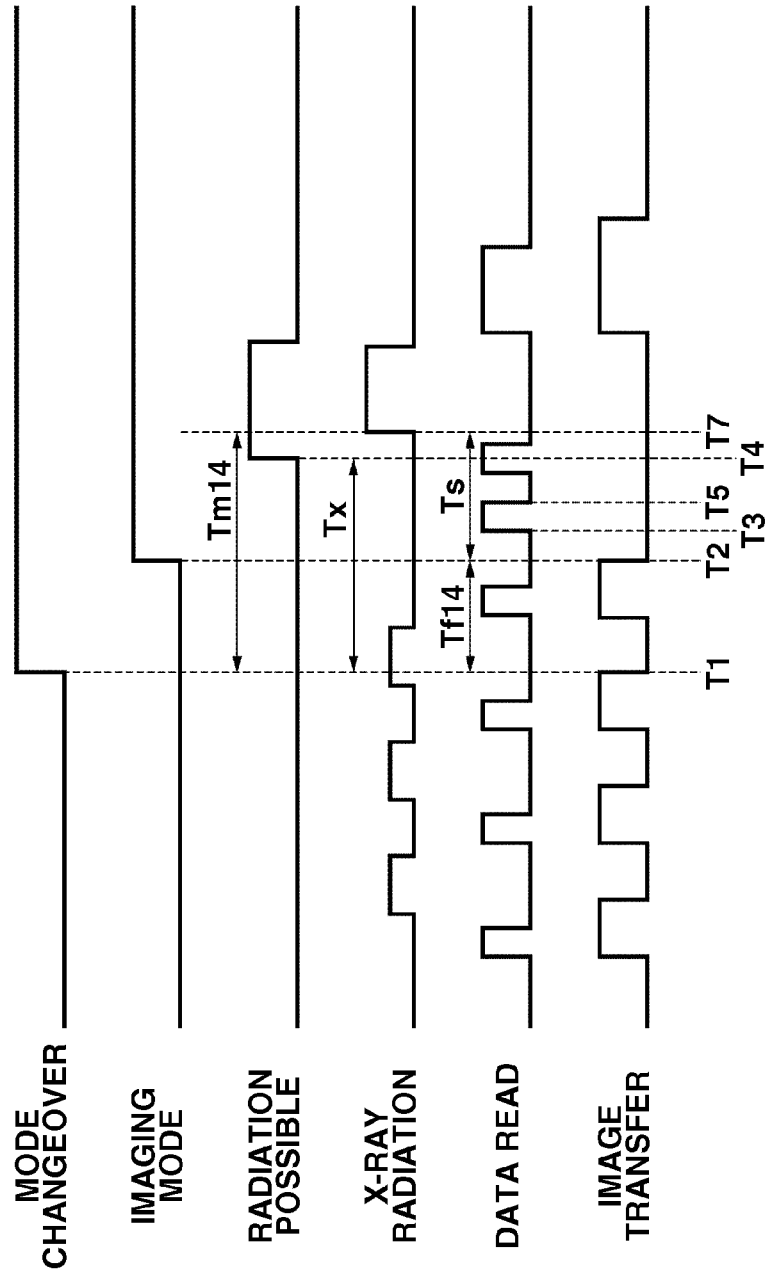

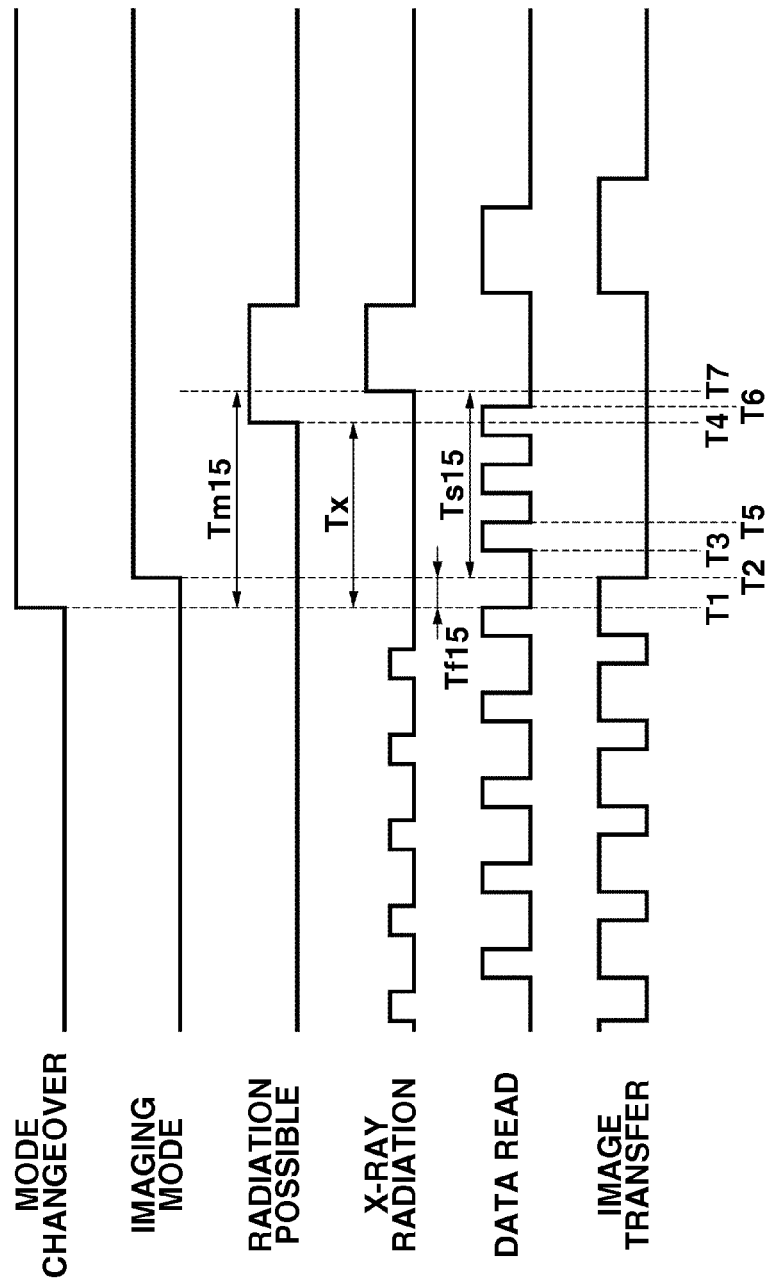

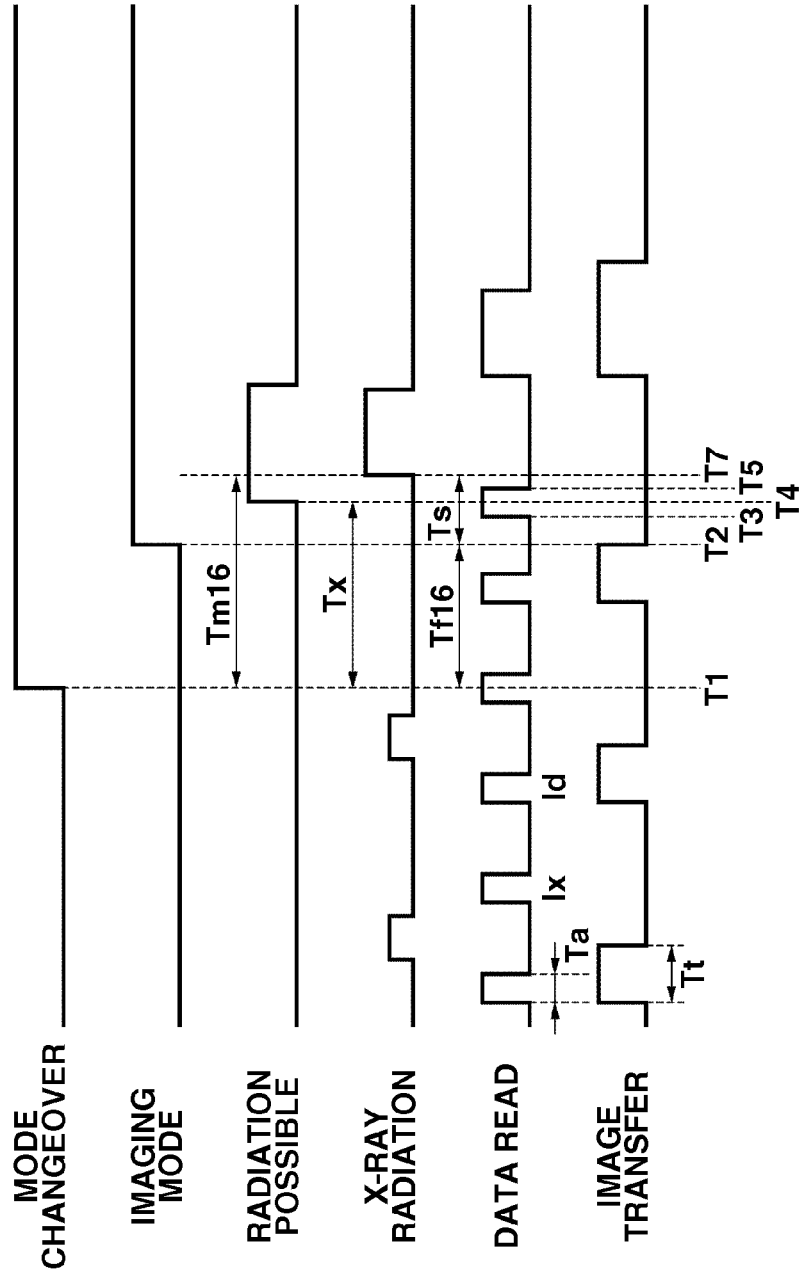

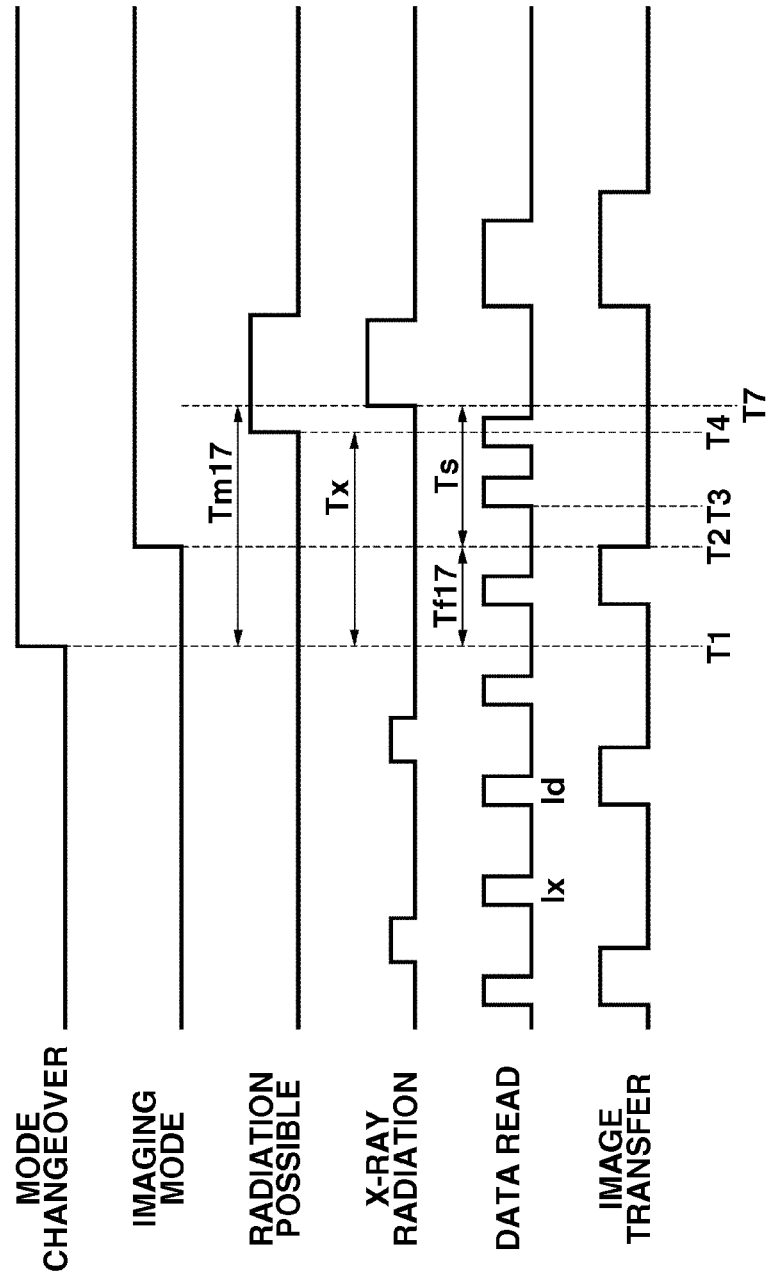

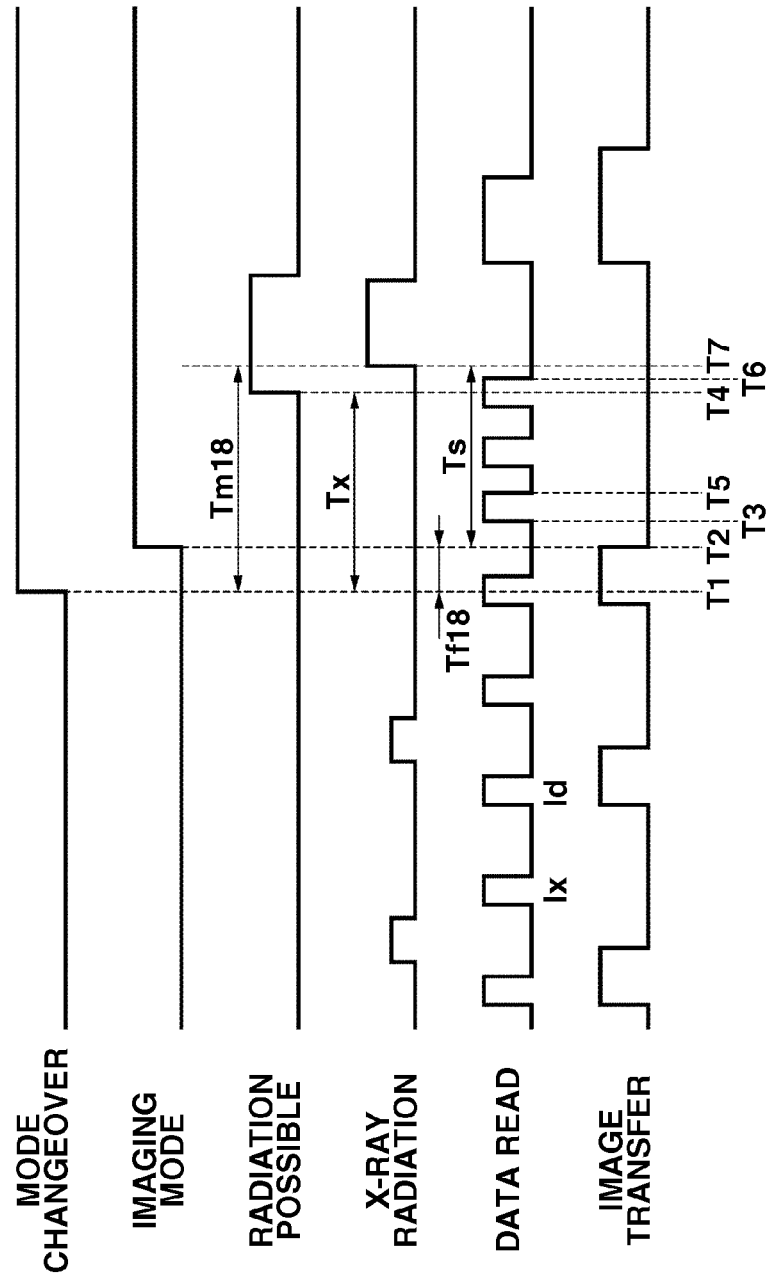

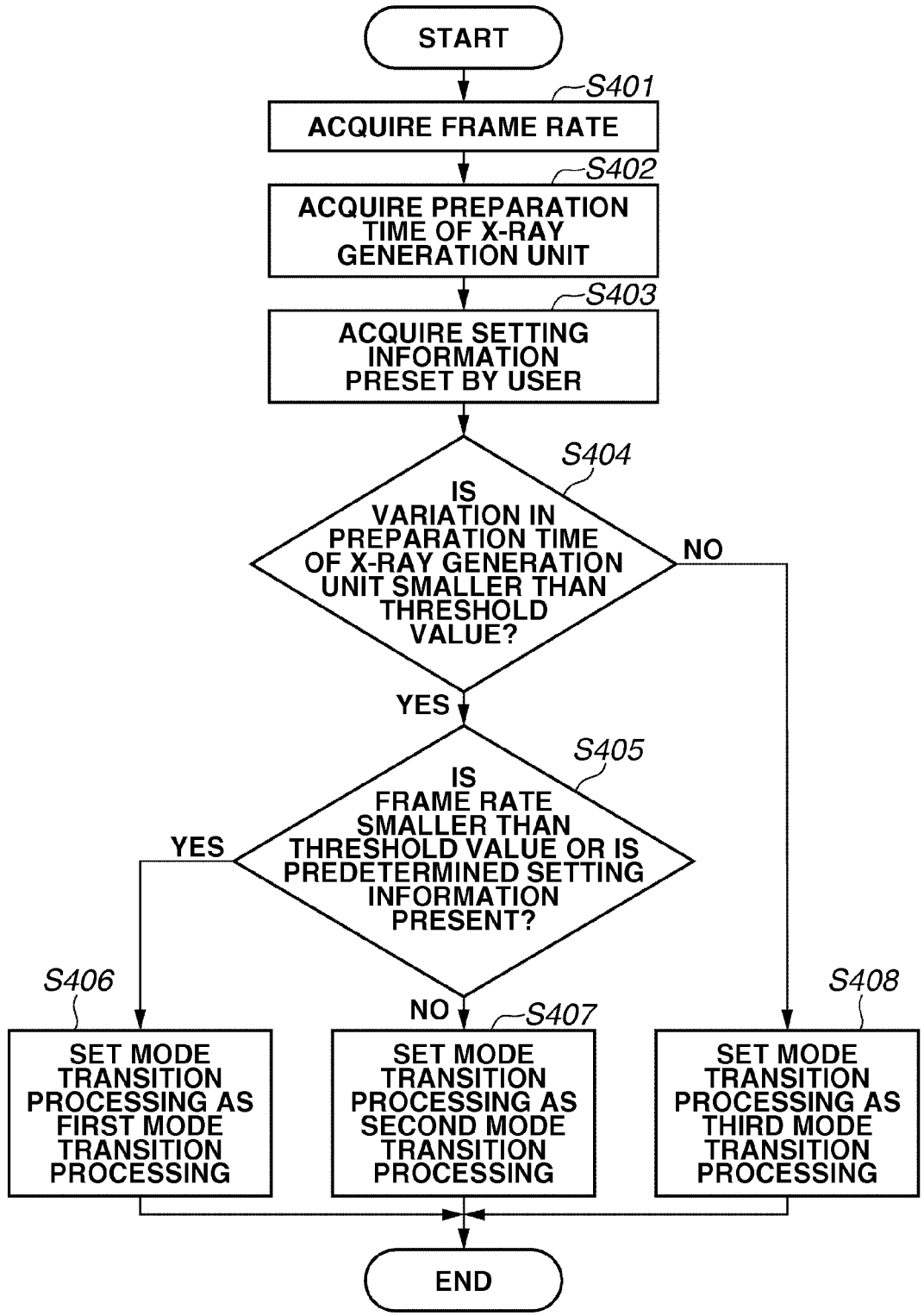

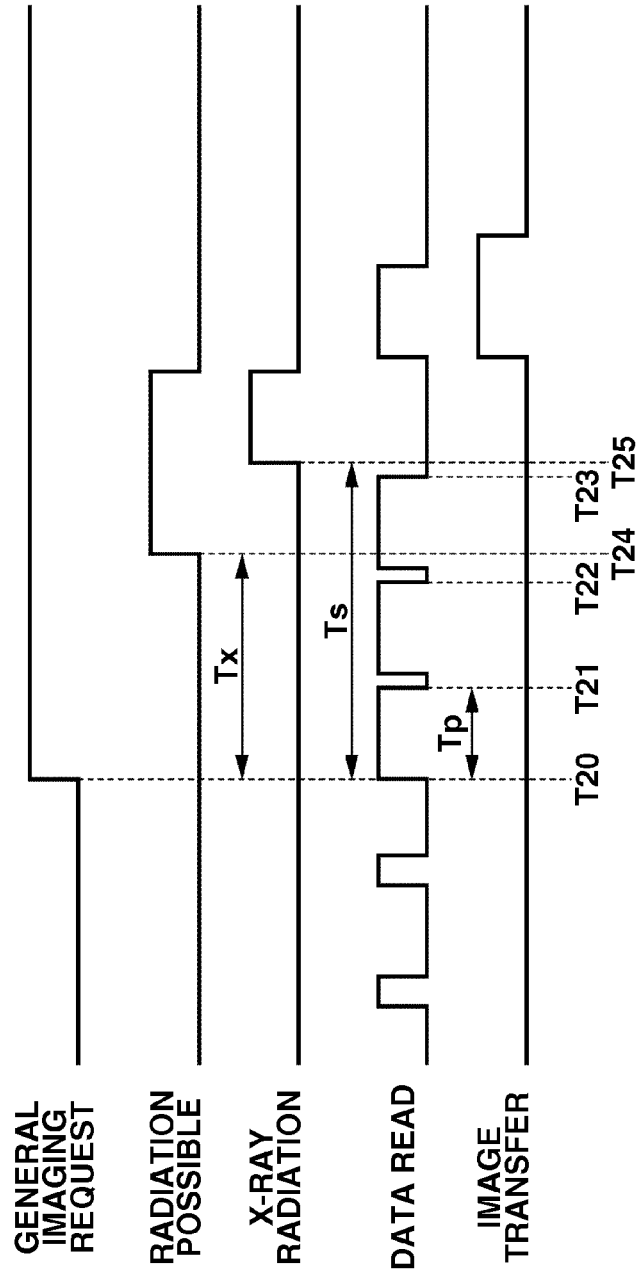

IMAGING CONTROL APPARATUS, RADIOGRAPHIC IMAGING SYSTEM, AND IMAGING CONTROL METHOD

BACKGROUND

The present disclosure relates to an imaging control apparatus, a radiographic imaging system, and an imaging control method.

Imaging systems using a sensor having sensitivity to visible light and radiation such as the X-ray are widely used in digital cameras and radiographic imaging systems for industrial and medical applications. An imaging system of this type such as an imaging apparatus discussed in Japanese Patent Application Laid-Open No. 2009-272673 is capable of capturing a moving image and a still image in a plurality of imaging modes according to its purpose. When changing the imaging mode, predetermined mode transition processing is sometimes required to change setting information and a sensor state. Japanese Patent Application Laid-Open No. 3-62500 discusses a technique for rotating a rotor of an X-ray generator and heating a cathode thereof during X-ray radioscopic imaging for subsequent still image capturing.

As another example, Japanese Patent Application Laid-Open No. 2000-292598 discusses a technique for waiting for a time longer than a frame rate immediately after moving image capturing and before transition from moving image capturing to still image capturing and then, immediately after the relevant wait time has elapsed, starting still image capturing.

Japanese Patent Application Laid-Open No. 2003-33340 discusses a technique for providing a wait time when a radiation switch for still image capturing is pressed in a non-imaging state.

SUMMARY

According to an embodiment of the present invention, a radiographic imaging apparatus includes a radiation detection array configured to store charges to acquire an image signal, an output unit configured to output radiation image data based on the image signal to an external apparatus, a detection unit configured to detect an imaging mode changeover instruction, and a control unit configured to, when the detection unit detects an imaging mode changeover instruction during one unit of imaging processing including the charge storage and the charge-based radiation image data output to an external apparatus, control whether the imaging processing is to be interrupted, based on an operating state of the radiographic imaging apparatus.

Further features and aspects of the embodiment will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the embodiment of the present invention.

FIG. 4 illustrates a table indicating a relation between a frame rate Fr and a decimal number in formula (1) according to the first exemplary embodiment.

FIG. 7 illustrates a table illustrating a relation between a frame rate Fr, a time Tf5max, and a time Tc represented by formula (2) according to the third exemplary embodiment.

FIG. 17 is a timing chart illustrating a case where a mode changeover request for switching from pulsed X-ray radioscopic imaging to general imaging is generated at a different timing.

FIG. 18 is a timing chart illustrating a case where a mode changeover request for switching from pulsed X-ray radioscopic imaging to general imaging is generated at a different timing.

FIG. 19 is a timing chart illustrating a case where a mode changeover request for switching from pulsed X-ray radioscopic imaging to general imaging is generated when a read operation is performed twice for one X-ray radiation.

FIG. 20 is a timing chart illustrating a case where a mode changeover request for switching from pulsed X-ray radioscopic imaging to general imaging is generated at a different timing when a read operation is performed twice for one X-ray radiation.

FIG. 21 is a timing chart illustrating a case where a mode changeover request for switching from pulsed X-ray radioscopic imaging to general imaging is generated at a different timing when a read operation is performed twice for one X-ray radiation.

FIG. 22 is a flowchart illustrating a flow of processing performed by an X-ray imaging system according to an eighth exemplary embodiment.

FIG. 23 is a timing chart for performing general imaging.

DESCRIPTION OF THE EMBODIMENTS

Various exemplary embodiments, features, and aspects of the invention will be described in detail below with reference to the drawings.

A first exemplary embodiment of the present invention will be described below.

In the first exemplary embodiment, for example, a first imaging mode is a pulsed X-ray radioscopic imaging mode which is a form of moving image capturing mode, and a second imaging mode is a general imaging (still image capturing) mode. Offset data is acquired in advance for offset correction.

Figure 1:
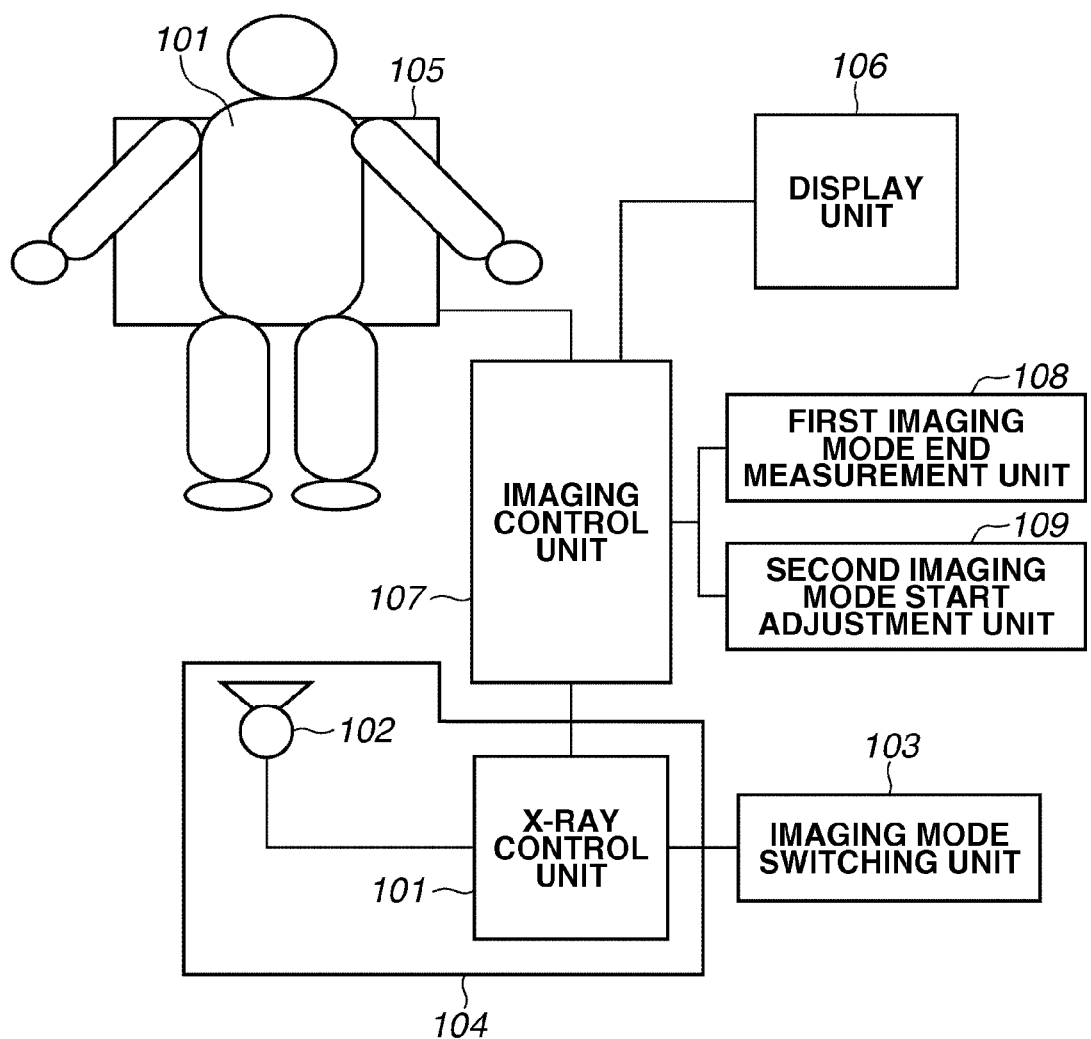
FIG. 1 is a schematic block diagram illustrating an X-ray imaging system according to a first exemplary embodiment.

FIG. 1 is a schematic block diagram illustrating an X-ray imaging system capable of performing pulsed X-ray radioscopic imaging and general imaging according to the embodiment of the present invention. The X-ray imaging system includes an X-ray generation unit (X-ray generator) 104 including an X-ray control unit 101 for controlling X-ray radiation to a subject 100, an X-ray tube 102 for actually radiating the X-ray, and an imaging mode switching unit 103. The X-ray tube 102 includes, for example, a rotating anode, a filament for X-ray radioscopic imaging, and a filament for general imaging (not illustrated).

The imaging mode switching unit 103 includes, for example, an X-ray radioscopic imaging switch and a general imaging switch (not illustrated) which are connected with the X-ray control unit 101. When an operator presses the X-ray radioscopic imaging switch, the X-ray imaging apparatus executes X-ray radioscopic imaging. When the operator presses the general imaging switch, it executes general imaging. When the operator presses the general imaging switch during X-ray radioscopic imaging, the X-ray control unit 101 determines that an imaging mode changeover request (hereinafter referred to as a mode changeover request) for switching from X-ray radioscopic imaging to general imaging is generated.

The X-ray imaging system includes an X-ray detection unit (X-ray detection apparatus) 105 for detecting the X-ray that has penetrated the subject 100. The X-ray detection unit 105 includes a phosphor for converting radiation into visible light, and a light detection array for detecting the converted visible light. The light detection array included in the X-ray detection unit 105 is an image sensor on which a number of detection elements (not illustrated) are arranged in matrix form. One detection element forms one pixel.

The X-ray detection unit 105 includes an X-ray image generation unit (not illustrated) for generating an X-ray image by sequentially reading charges stored in the detection elements, and a transfer unit (not illustrated) for transferring the generated X-ray image. The X-ray imaging system further includes a display unit 106 for displaying the X-ray image read from the X-ray detection unit 105, and an imaging control unit 107 for controlling the entire X-ray imaging system.

The imaging control unit 107 includes an image storage unit (not illustrated) for storing captured images.

The imaging control unit 107 further includes a first imaging mode end measurement unit 108 and a second imaging mode start adjustment unit 109. The first imaging mode end measurement unit 108 measures a time since an imaging mode changeover occurs until the X-ray radioscopic imaging mode ends. According to the result of measurement, the second imaging mode start adjustment unit 109 adjusts the time since the X-ray radioscopic imaging mode ends until the general imaging mode starts.

The imaging control unit 107 may be configured as an apparatus different from the X-ray generation unit 104 and the X-ray detection unit 105, and sometimes referred to as an imaging control apparatus or a control apparatus in the present exemplary embodiment. A first imaging mode is sometimes referred to as a current imaging mode, and a second imaging mode is sometimes referred to as a following imaging mode.

Figure 2:
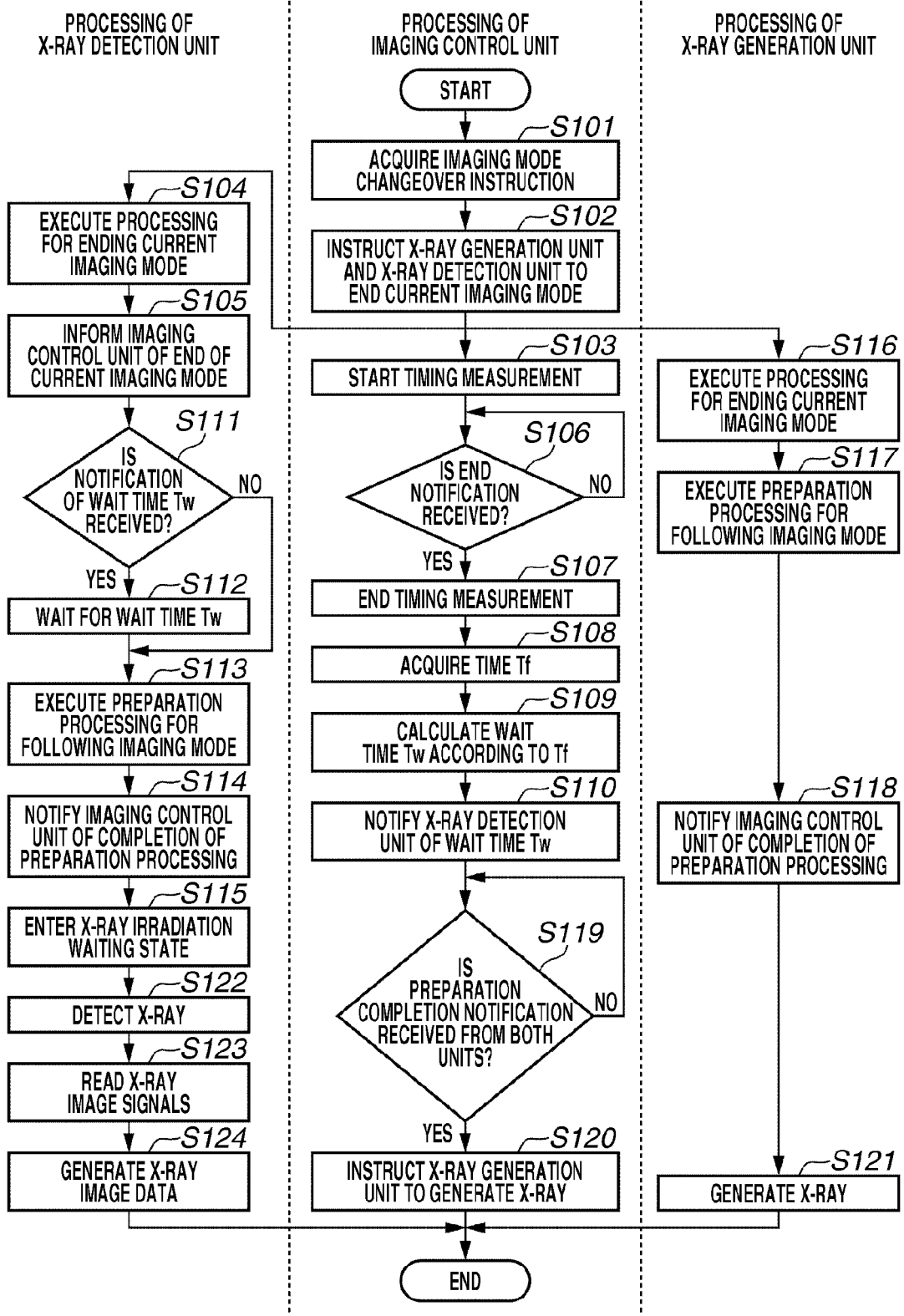
FIG. 2 is a flowchart illustrating a flow of processing performed by the X-ray imaging system according to the first exemplary embodiment.

A flow of processing according to the present exemplary embodiment will be described below with reference to FIG. 2. The processing described below relates to the mode transition processing performed by the X-ray generation unit 104 and the X-ray detection unit 105 in response to a mode changeover instruction from the imaging mode switching unit 103. In the mode transition processing, the imaging control unit 107 performs control for instructing the imaging system to end the first imaging mode, and control for instructing the imaging system to prepare for execution of the second imaging mode.

Control of the first imaging mode, i.e., X-ray radioscopic imaging will be described below. The imaging control unit 107 controls the X-ray detection unit 105 so that the storage operation, image signal read operation, and image data transfer operation are completed within one frame duration determined by a preset frame rate. The imaging control unit 107 outputs the X-ray radiation enabling signal to the X-ray control unit 101 during a period from start to end of the storage operation. The imaging control unit 107 does not output the X-ray radiation enabling signal except for a period from start to end of the storage operation.

The X-ray control unit 101 controls the X-ray tube 102 to perform X-ray irradiation based on a predetermined frame rate and irradiation conditions. The X-ray control unit 101 detects a rising edge of the X-ray radiation enabling signal to control the X-ray tube 102. After X-ray irradiation, the X-ray control unit 101 does not perform X-ray irradiation until the X-ray radiation enabling signal rises again. Thus, pulsed X-ray radioscopic imaging can be achieved while preventing invalid X-ray radiation except for a period of the storage operation duration.

X-ray radioscopic imaging can also be achieved when the imaging control unit 107 controls the operation timing of the X-ray detection unit 105 to enable the X-ray detection unit 105 to perform the storage operation at least during the pulsed X-ray irradiation period based on the information about predetermined frame rate and pulse width. In another example, the X-ray detection unit 105 detects the X-ray irradiation state based on the charges stored therein to control the operation of the X-ray detection unit 105, thus achieving X-ray radioscopic imaging.

In step S101, the imaging control unit 107 receives an instruction signal from the imaging mode switching unit 103 to acquire a mode changeover instruction. Specifically, the imaging control unit 107 detects that an instruction for executing the second imaging mode is generated during execution of the first imaging mode.

In step S102, the imaging control unit 107 instructs the X-ray generation unit 104 and the X-ray detection unit 105 to end the imaging mode currently being executed. The instruction for ending the imaging mode serves as a control signal for instructing to start a mode transition, more specifically, a control signal for instructing to end the current imaging mode, and a control signal for instructing to prepare for the following imaging mode. In other words, the imaging control unit 107 performs control for ending the first imaging mode in response to the relevant instruction. Immediately after this control, in step S103, the first imaging mode end measurement unit 108 of the imaging control unit 107 measures a time required for the X-ray detection unit 105 to end the current imaging mode. Specifically, the first imaging mode end measurement unit 108 measures a time since the relevant instruction is detected until the first imaging mode ends.

In step S104, the X-ray detection unit 105 performs processing for ending the current imaging mode in response to an instruction from the imaging control unit 107. During X-ray radioscopic imaging, the X-ray detection unit 105 may be in different states such as an X-ray detecting state, an electrical signal reading state, a dark current storing state, an X-ray image transferring state, and so on. When one unit of an imaging and image transfer process ends, the X-ray detection unit 105 ends X-ray radioscopic imaging. Therefore, the time measured by the imaging control unit 107 changes according to the timing of instruction. In step S105, the X-ray detection unit 105 informs the imaging control unit 107 that the current imaging mode has ended.

In step S106, the imaging control unit 107 waits for reception of a notification that the current imaging mode has ended, from the X-ray detection unit 105. Upon reception of the notification that the current imaging mode has ended (YES in step S106), then in step S107, the first imaging mode end measurement unit 108 of the imaging control unit 107 ends timing measurement. In step S108, the imaging control unit 107 acquires a time Tf measured by the first imaging mode end measurement unit 108. The time Tf corresponds to a time since a mode changeover instruction is generated until the current imaging mode ends.

In step S109, the imaging control unit 107 determines a wait time Tw according to the time Tf. Specifically, the imaging control unit 107 determines the wait time Tw according to the state of the imaging system when the relevant instruction is received and then determines the wait time Tw according to the measured time. The wait time Tw compensates a change in the measured time Tf to make constant a time since the imaging mode is changed by an imaging mode changeover instruction (hereinafter referred to as a mode changeover instruction) until imaging in the following imaging mode is started. The time is not necessarily required to be constant because of the influence of a mode transition of the X-ray generation unit 104. Therefore, the wait time Tw is set to reduce variation in time required for a mode transition.

Further, when the mode transition time of the X-ray generation unit 104 varies, it is possible that the wait time Tw serves to compensate the relevant variation. Variation in the mode transition time of the X-ray generation unit 104 is grasped with an appropriate accuracy and previously stored in memory, and the wait time Tw is set in consideration of the maximum and average values of the mode transition time to cause the X-ray detection unit 105 to stand by. For example, the wait time Tw is set so that the mode transition of the X-ray detection unit 105 ends within a time equal to the average of the mode transition time of the X-ray generation unit 104. Specifically, according to the operating state of the imaging system when the relevant instruction is received, the imaging control unit 107 determines the wait time Tw so that the time since the instruction is generated until imaging mode transition ends, becomes close to a fixed value regardless of the timing at which the instruction is received.

The wait time Tw may be determined by using a predefined formula or a lookup table for determining the wait time Tw corresponding to the value of the time Tf. The imaging control unit 107 determines the different wait time Tw depending on a situation. Examples of situations include a case where an instruction is received while the image sensor of the imaging system is storing an electrical signal according to detected light or radiation, a case where an instruction is received while the image sensor is reading an electrical signal, and a case where an instruction is received during transfer of data based on the read electrical signal.

In step S110, the imaging control unit 107 notifies the X-ray detection unit 105 of the wait time Tw. This notification serves as a control signal for instructing the X-ray detection unit 105 to start waiting, and a control signal for instructing the X-ray detection unit 105 to start mode transition processing (described below) after the waiting. Specifically, the imaging control unit 107 performs control for instructing the X-ray detection unit 105 to wait at least for the determined wait time Tw before the transition to the second imaging mode, and control for instructing the X-ray detection unit 105 to perform the mode transition processing for switching from the first imaging mode to the second imaging mode. The wait time Tw is sometimes set to 0 depending on the situation. In this case, the imaging control unit 107 transfers a signal for notifying the X-ray detection unit 105 that Tw=0.

In step S111, the X-ray detection unit 105 waits for reception of the relevant notification about the wait time Tw. Upon reception of the relevant notification about the wait time Tw (YES in step S111), the processing proceeds to step S112. Otherwise (NO in step S111), if the relevant notification is not received within a fixed period of time, the processing proceeds to step S113. In this processing, the mode transition is prevented from being disabled in the event of a signal exchange failure due to a communication error. In step S112, the X-ray detection unit 105 waits, for the wait time Tw. During the wait time Tw, the X-ray detection unit 105 does not perform any operation such as a discharging operation.

In step S113, the X-ray detection unit 105 performs preparation processing for executing the imaging mode related to the relevant instruction from the imaging mode switching unit 103. The preparation processing includes processing for discharging an image lag signal and a dark current signal stored in the X-ray detection unit 105. When using metal insulator semiconductor (MIS) type photoelectric conversion elements, the preparation processing includes processing for removing holes or electrons stored in the element to enable storing photoelectric charges. The preparation processing further includes processing for changing amplifier's gain accompanying an imaging mode changeover.

In step S114, after completion of the preparation processing, the X-ray detection unit 105 notifies the imaging control unit 107 that the preparation is completed and it has become ready for the following imaging mode. After notification, in step S115, the X-ray detection unit 105 enters the X-ray irradiation waiting state. When performing as preparation the processing for discharging a dark current signal stored over time, the X-ray detection unit 105 repeats the dark current discharge processing at fixed intervals even after completion of the relevant preparation processing.

In the meantime, in step S116, the X-ray generation unit 104 performs the processing for ending the current imaging mode in response to the imaging mode end instruction. As described above, in the present exemplary embodiment, even when a mode changeover instruction is generated during one-unit imaging, the X-ray generation unit 104 ends the relevant one-unit imaging and then enters the following imaging mode. In step S117, the X-ray generation unit 104 performs X-ray irradiation preparation processing according to settings of the tube voltage, tube current, irradiation time, etc., for the following imaging mode. After completion of the X-ray irradiation preparation processing, in step S118, the X-ray generation unit 104 notifies the imaging control unit 107 that the X-ray irradiation preparation processing is completed.

In step S119, the imaging control unit 107 waits for reception of a preparation completion notification from both the X-ray generation unit 104 and the X-ray detection unit 105. Upon reception of the relevant notification from both the X-ray generation unit 104 and the X-ray detection unit 105 (YES in step S119), then in step S120, the imaging control unit 107 instructs the X-ray generation unit 104 to generate the X-ray based on the settings related to the imaging mode after mode changeover.

In step S121, the X-ray generation unit 104 generates the X-ray in response to the X-ray generation instruction. In step S122, the X-ray detection unit 105 detects the X ray which is generated by the X-ray generation unit 104 and has penetrated the subject, and each pixel of the X-ray detection unit 105 generates an electrical signal according to the intensity of the X-ray.

Figure 3:
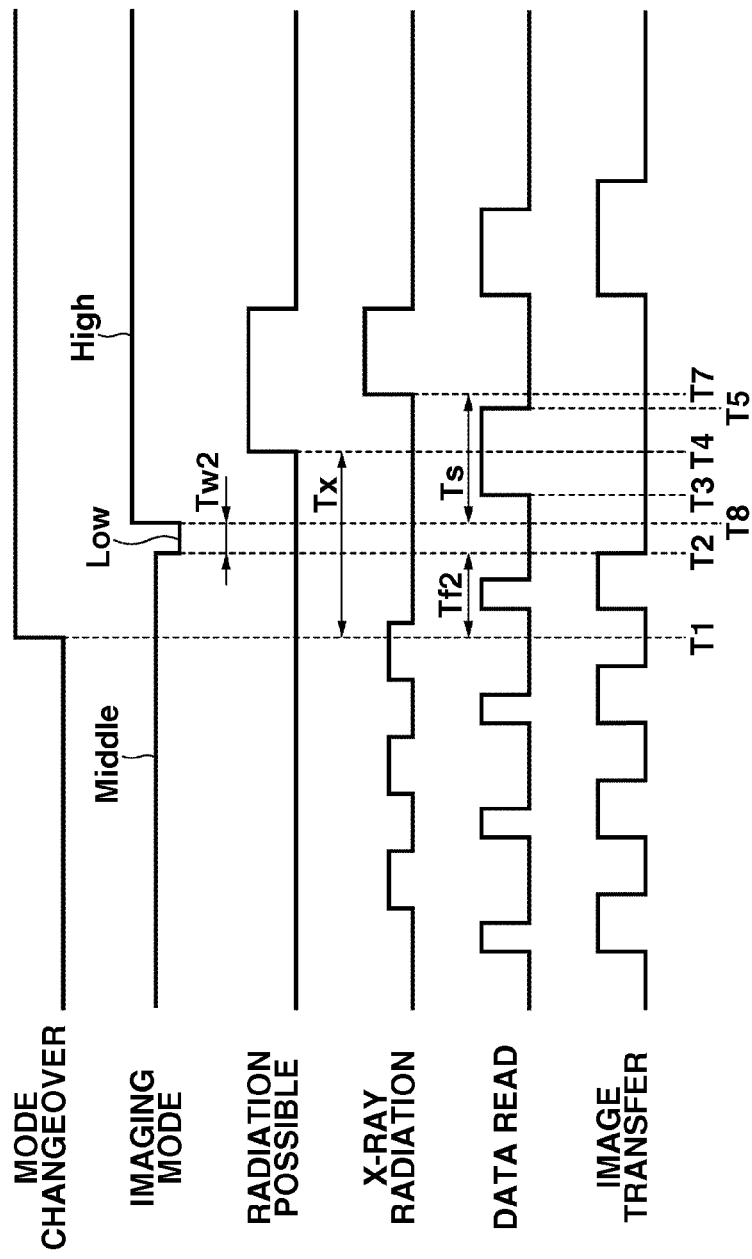
FIG. 3 is a timing chart illustrating a case where a mode changeover request for switching from pulsed X-ray radioscopic imaging to general imaging is generated, according to the first exemplary embodiment.

In step S123, the X-ray detection unit 105 sequentially reads electrical signals generated by pixels through respective signal lines. In step S124, the X-ray detection unit 105 amplifies the read electrical signals by using an amplifier and then converts analog signals into digital form by using an analog-to-digital (AD) converter to generate X-ray image data. The first imaging mode end measurement unit 108 and the second imaging mode start adjustment unit 109 will be described in detail below. FIG. 3 is an example of a timing chart illustrating a case where a mode changeover request for switching from pulsed X-ray radioscopic imaging to general imaging is made.

Referring to FIG. 3, the mode changeover instruction for switching from pulsed X-ray radioscopic imaging to general imaging indicates a case where a mode changeover instruction is generated during X-ray radiation by the X-ray generation unit 104.

Referring to FIG. 3, the Low level indicates wait processing when switching from X-ray radioscopic imaging to general imaging, the Middle level indicates the X-ray radioscopic imaging mode, and the High level indicates the general imaging mode. The first imaging mode end measurement unit 108 and the second imaging mode start adjustment unit 109 are controlled by the imaging control unit 107 to perform wait processing when switching from X-ray radioscopic imaging to general imaging.

The timing chart illustrated in FIG. 3 will be described below.

When the X-ray generation unit 104 notifies the imaging control unit 107 that a mode changeover request is generated, the imaging control unit 107 measures a time until X-ray radioscopic imaging ends, by using the first imaging mode end measurement unit 108 included in the imaging control unit 107. For example, the first imaging mode end measurement unit 108 including a timer starts the timer at a time T1 at which an imaging mode changeover occurs. At a time T2 at which the first imaging mode end measurement unit 108 receives the last X-ray radioscopic image transferred from the X-ray detection unit 105, the first imaging mode end measurement unit 108 stops the timer and measures a time Tf2 until X-ray radioscopic imaging ends.

Then, the second imaging mode start adjustment unit 109 performs wait processing when switching from X-ray radioscopic imaging to general imaging according to the measured time Tf2 and then starts general imaging. The imaging control unit 107 outputs, for example, an X-ray radiation enabling signal for general imaging to the X-ray generation unit 104. Upon reception of the relevant signal, the X-ray generation unit 104 starts X-ray radiation for general imaging.

After completion of X-ray radiation for general imaging, the X-ray generation unit 104 reads charges from the X-ray detection elements, performs offset correction, and then transfers the read image to the imaging control unit 107. Upon reception of the image captured in general imaging, the imaging control unit 107 displays the image on the display unit 106. Offset correction for general imaging is similar to offset correction for X-ray radioscopic imaging. An X-ray image is acquired by subtracting general imaging data acquired in advance without X-ray radiation from the data read immediately after X-ray radiation.

A wait time Tw2 during which the second imaging mode start adjustment unit 109 waits is a time from the time T2 to a time T8. The second imaging mode start adjustment unit 109 calculates the wait time Tw2 by using the following formula (1).

$$Tw2 = Tx - Tf2 - a*Ts (a \leq 1.0) \quad (1)$$

where Tx indicates a time from the time T1 at which a mode changeover request is generated, to a time T4 at which the X-ray generation unit 104 becomes ready for executing general imaging, Ts indicates a time from the time T8 at which general imaging is selected after the wait time Tw2 (during which the second imaging mode start adjustment unit 109 waits), to the time T7 at which the X-ray generation unit 104 starts X-ray radiation for general imaging, and a indicates a decimal number satisfying the condition described in formula (1). The decimal number a in formula (1) will be described below.

The maximum value of the time Tf2 measured by the first imaging mode end measurement unit 108 depends on a frame rate Fr for X-ray radioscopic imaging (hereinafter referred to as an X-ray radioscopic imaging frame rate Fr), i.e., the maximum value is a reciprocal of the X-ray radioscopic frame rate Fr. For example, when the X-ray radioscopic imaging frame rate Fr=10, the maximum value of the time Tf2 is 100 ms. When the X-ray radioscopic imaging frame rate Fr=5, the maximum value thereof is 200 ms.

The X-ray generation unit 104 other than that discussed in Japanese Patent Application Laid-Open No. 2003-33340 will be described below. When a mode changeover request for switching from X-ray radioscopic imaging to general imaging is generated, it takes the time Tx since X-ray radioscopic imaging ends until general imaging is enabled. Since the time Tx varies, an increase in the time Tx increases the number of reset operations for erasing an image lag which occurs during X-ray radioscopic imaging, as described above with reference to FIG. 18. As a result, the time for switching from X-ray radioscopic imaging to general imaging is prolonged.

Therefore, the decimal number a serves as a coefficient for preventing the number of reset operations from increasing. For example, when the X-ray radioscopic imaging frame rate Fr=10, the reset operation time Tp=300 ms, the number of reset operations=1, and the X-ray generation unit 104 based on a method (Tx=400±30 ms) discussed in Japanese Patent Application Laid-Open No. 2000-292598, the decimal number a=about 0.8 is desirable. When the X-ray generation unit 104 is based on a general method (Tx=1000 m±100 ms), the decimal number a=about 0.5 is desirable.

Thus, even if the time Tx varies, the X-ray generation unit 104 can prepare for X-ray radiation for general imaging while the X-ray detection unit 105 is performing one reset operation. However, if an image lag which occurs during X-ray radioscopic imaging does not disappear in the one reset operation, the X-ray detection unit 105 needs to perform the reset operation a plurality of number of times. In this case, it is preferable to determine the decimal number a according to the number of reset operations. Since, determining the X-ray generation unit 104 used by the X-ray imaging apparatus determines the time Tx and determining the X-ray detection unit 105 determines the time Ts, the second imaging mode start adjustment unit 109 previously stores the time Tx, the time Ts, and the decimal number a in memory. The time Tx may be set from an external setting unit according to the X-ray generation unit 104.

However, when the X-ray radioscopic imaging frame rate Fr=5, if the X-ray generation unit 104 is based on a method discussed in Japanese Patent Application Laid-Open No. 2000-292598, and the decimal number=0.8 (similar to the case where the frame rate Fr=10), the value of the wait time Tw2 calculated by formula (1) becomes negative. To avoid this, it is necessary to set the decimal number a, for example, to 0.5. Therefore, preferably, the decimal number a may have a different value for each X-ray radioscopic imaging frame rate Fr.

For example, when the X-ray radioscopic imaging frame rate Fr≥10, the decimal number may be fixed to 0.8. Otherwise, when the X-ray radioscopic imaging frame rate Fr<10, the decimal number may be set to a small value for each frame rate Fr.

An example of a relation between the frame rate Fr and the decimal number a in the case of the X-ray generation unit 104 (Tx=400±30 ms) is illustrated in FIG. 4. In this case, when the X-ray radioscopic imaging frame rate Fr≥10, the time for switching from X-ray radioscopic imaging to general imaging is constant. Otherwise, when the frame rate Fr<10, the time for switching from X-ray radioscopic imaging to general imaging is prolonged depending on the frame rate Fr. However, for example, when the X-ray radioscopic imaging frame rate Fr=5, the time for switching from X-ray radioscopic imaging to general imaging is constant.

As mentioned above, when a mode changeover request is generated, the first imaging mode end measurement unit 108 measures a time Tf2 until the X-ray radioscopic imaging ends. Accordingly, the second imaging mode start adjustment unit 109 adjusts the wait time Tw2 until general imaging starts. Therefore, the shorter the measured time Tf2, the longer the wait time Tw2 calculated by formula (1). Conversely, the longer the measured time Tf2, the shorter the wait time Tw2 calculated by formula (1). Specifically, if the X-ray radioscopic imaging frame rate Fr is high, a time since a mode changeover request for switching from X-ray radioscopic imaging to general imaging is generated until general imaging is executed, becomes constant.

Although, in the first exemplary embodiment, the imaging mode switching unit 103 includes the X-ray radioscopic imaging switch and the general imaging switch which are connected with the X-ray control unit 101, an exemplary embodiment is not limited thereto. For example, the imaging control unit 107 may include a touch panel which is operated by an operator.

Although, in the first exemplary embodiment, the imaging control unit 107 includes the first imaging mode end measurement unit 108 and the second imaging mode start adjustment unit 109, the configuration is not limited thereto. For example, these two units may be included in the X-ray detection unit 105.

Although, in the first exemplary embodiment, the first imaging mode denotes pulsed X-ray radioscopic imaging and the second imaging mode denotes general imaging, an exemplary embodiment is not limited thereto. It is possible that the first imaging mode denotes pulsed serial imaging and the second imaging mode denotes general imaging, or that the first imaging mode denotes pulsed X-ray radioscopic imaging and the second imaging mode denotes pulsed serial imaging.

Although, in the first imaging mode, the first imaging mode denotes pulsed X-ray radioscopic imaging and the second imaging mode denotes general imaging, an exemplary embodiment is not limited thereto. Moving image may be captured by X-ray radioscopic imaging or continuous serial imaging.

A second exemplary embodiment of the present invention will be described below.

In the second exemplary embodiment, an X-ray imaging apparatus has a similar configuration to the X-ray imaging apparatus according to the first exemplary embodiment, and the first imaging mode denotes pulsed X-ray radioscopic imaging and the second imaging mode denotes general imaging. However, the X-ray generation unit 104 has a long changeover time Tx for switching from X-ray radioscopic imaging to general imaging. As an example, a case where the time Tx=1000 m±200 and the X-ray radioscopic imaging frame rate Fr=10 will be described below.

In the first exemplary embodiment, when the X-ray radioscopic imaging frame rate Fr=10, the decimal number a=0.8. However, in the second exemplary embodiment, when the time Tx is prolonged, a wait time Tw4 from the time T2 to the time T8 also is prolonged, referring to FIG. 5. Since the time Tx largely varies, the X-ray generation unit 104 sometimes is not ready for executing general imaging when the reset operation for erasing an image lag which occurs in the X-ray radioscopic imaging mode, is completed. In this case, the X-ray detection unit 105 performs a second reset operation. As a result, the changeover time Ts from X-ray radioscopic imaging to general imaging is prolonged.

For example, when the decimal number is set to a small value of 0.1, performing reset operation once is sufficient. In this case, however, the wait time Tw4 during which the second imaging mode start adjustment unit 109 waits is always prolonged. As a result, the time for switching from X-ray radioscopic imaging to general imaging is prolonged.

Figure 5:
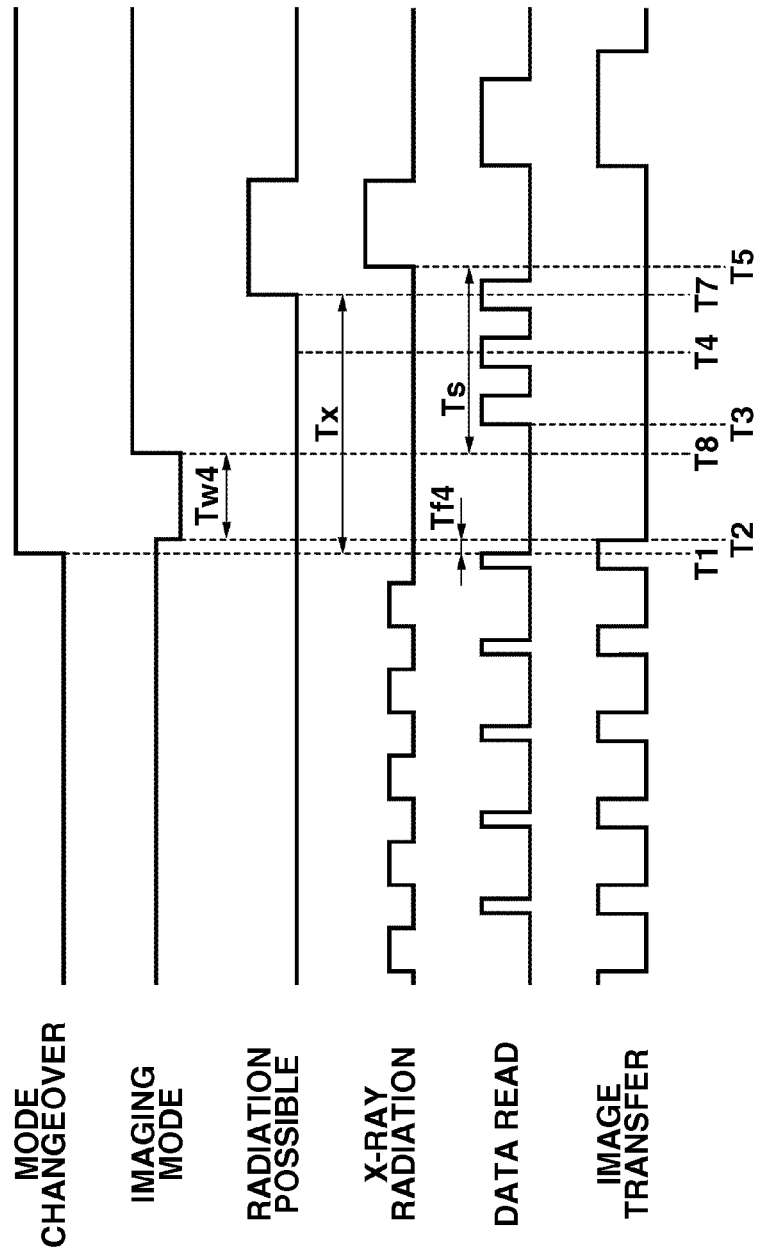
FIG. 5 is a timing chart illustrating a case where a mode changeover request for switching from pulsed X-ray radioscopic imaging to general imaging is generated, according to a second exemplary embodiment.

To avoid this, it is preferable to shorten the reset operation for erasing an image lag. FIG. 5 is a timing chart illustrating a case where the reset operation time is shortened.

Referring to FIG. 5, since the reset operation time is short, it is necessary to increase the number of reset operations. However, even if the time Tx is prolonged and the number of reset operations increases, the time for switching from X-ray radioscopic imaging to general imaging prolonged thereby can be shortened.

A method for shortening the reset operation will be described below. Instead of resetting the detection elements of the X-ray detection unit 105 row by row, if the resetting is performed in units of a plurality number of rows (for example, two rows), the operation time for erasing an image lag is halved, i.e., about 150 ms. Further, if the resetting is performed in units of three rows, the reset operation time is a third, i.e., about 100 ms.

Further, instead of performing the operation for erasing an image lag in the same time as a time for reading one row for general imaging, if the relevant operation is performed in the same time as a time for reading one row for X-ray radioscopic imaging, the reset operation for erasing an image lag can be performed in the same time as the read time during X-ray radioscopic imaging, i.e., about 20 ms.

Although, in the second exemplary embodiment, the X-ray radioscopic imaging frame rate Fr=10, it is not limited thereto and may be, for example, 20. Other configurations are similar to those of the first exemplary embodiment.

A third exemplary embodiment of the present invention will be described below.

In the third exemplary embodiment, an X-ray imaging apparatus has a similar configuration to the X-ray imaging apparatus according to the first exemplary embodiment except that the imaging mode switching unit 103 is different, and the X-ray generation unit 104 is similar to an X-ray generation unit discussed in Japanese Patent Application Laid-Open No. 2003-33340. In this case, the changeover time Tx of the X-ray generation unit 104 for switching from X-ray radioscopic imaging to general imaging is so short that it can be ignored. Similar to the first exemplary embodiment, the first imaging mode denotes pulsed X-ray radioscopic imaging and the second imaging mode denotes general imaging.

Figure 6:
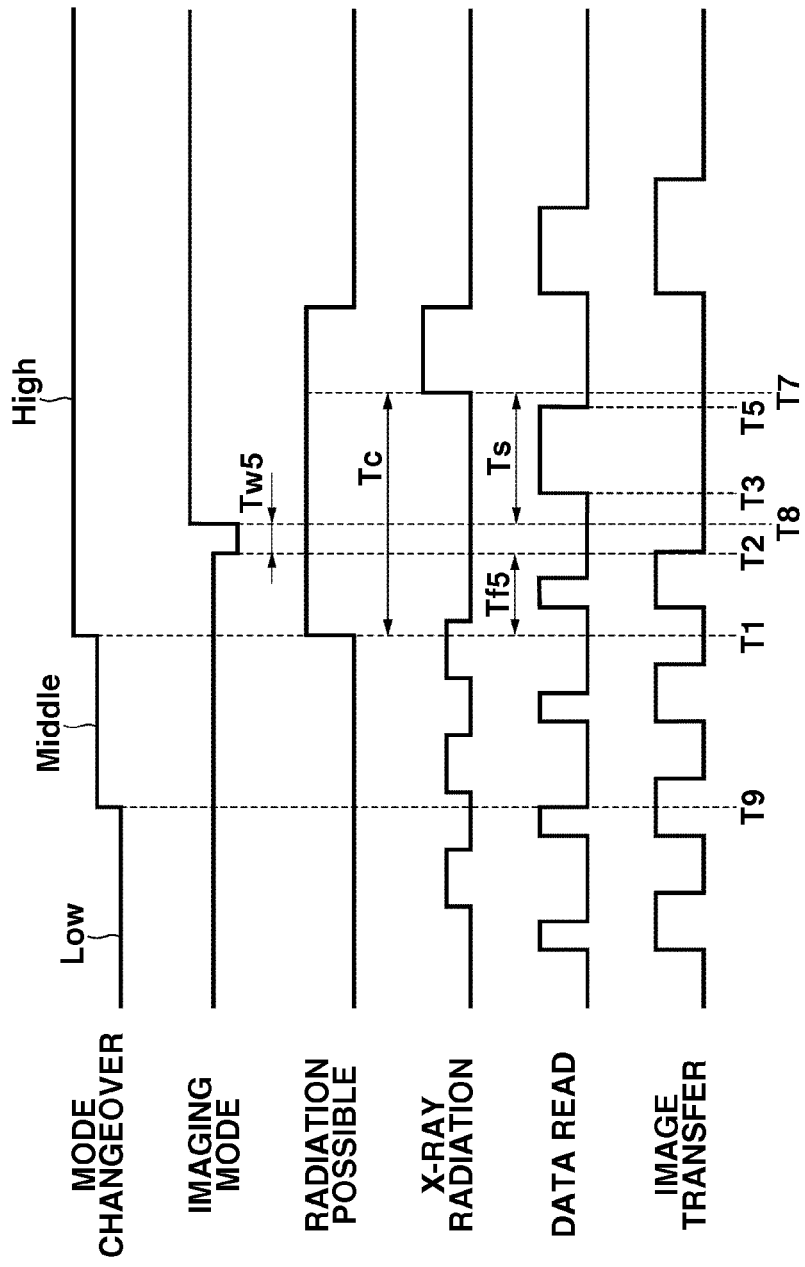
FIG. 6 is a timing chart illustrating a case where a mode changeover request for switching from pulsed X-ray radioscopic imaging to general imaging is generated, according to a third exemplary embodiment.

FIG. 6 is a timing chart according to the third exemplary embodiment.

Similar to the first exemplary embodiment, the imaging mode switching unit 103 according to the third exemplary embodiment includes the X-ray radioscopic imaging switch and the general imaging switch which are connected with the X-ray control unit 101. For example, when the operator presses the X-ray radioscopic imaging switch, the X-ray imaging apparatus executes X-ray radioscopic imaging. When the operator presses the general imaging switch, it executes general imaging. However, when the operator presses the general imaging switch during X-ray radioscopic imaging, at a time T9, the X-ray generation unit 104 starts the preparation for executing general imaging while performing X-ray radioscopic imaging.

The preparation for general imaging is an operation for erasing an image lag which occurs in the X-ray radioscopic imaging mode. For example, the X-ray detection unit 105 performs the reset operation for the detection elements row by row as discussed in Japanese Patent Application Laid-Open No. 2009-272673. Since this operation is almost the same as the data read operation, data is read at the High level. Then, at the time T1, when the X-ray generation unit 104 has become ready for general imaging during X-ray radioscopic imaging, the X-ray generation unit 104 determines that a mode changeover request for switching from X-ray radioscopic imaging to general imaging is generated.

Referring to FIG. 6, the meaning of mode changeover according to the present exemplary embodiment is different from that according to the first exemplary embodiment, as described below. The Low level indicates a state where the X-ray generation unit 104 is performing X-ray radioscopic imaging. The Middle level indicates a state where, after the general imaging switch is pressed during X-ray radioscopic imaging, the X-ray generation unit 104 is performing the preparation operation for general imaging during X-ray radioscopic imaging. The High level indicates a state where the X-ray generation unit 104 has become ready for general imaging and then a mode changeover request for switching from X-ray radioscopic imaging to general imaging is generated.

The second imaging mode start adjustment unit 109 according to the present exemplary embodiment is different from that according to the first exemplary embodiment. The difference will be described below. In the first exemplary embodiment, Tx indicates a time from the time T1 at which a mode changeover request is generated to the time T4 at which the X-ray generation unit 104 becomes ready for general imaging. In the third exemplary embodiment, since the time at which the X-ray generation unit 104 becomes ready for general imaging is recognized as the time at which a mode changeover request is generated, the time Tx=0. Therefore, a time Tc is introduced instead of the time Tx.

The time Tc is calculated with the following formula (2), where Tf5max indicates a maximum time since a mode changeover request is generated until X-ray radioscopic imaging ends, and Ts indicates a time from the time T8 at which general imaging is selected to the time T7 at which the X-ray generation unit 104 starts X-ray radiation for general imaging.

$$Tc = Tf5\max + Ts \quad (2)$$

When the X-ray radioscopic imaging frame rate Fr=10, Tf5max=100 ms. When the reset operation time Tp=300 ms, the time Ts=300 ms. Therefore, the time Tc=400 ms.

By using the time Tc calculated by formula (2), a wait time Tw5 during which the second imaging mode start adjustment unit 109 waits when switching from X-ray radioscopic imaging to general imaging is calculated with the following formula (3).

$$Tw5 = Tc - Tf5 - Ts \quad (3)$$

where Tf5 indicates a time, measured by the first imaging mode end measurement unit 108, from the time T1 at which an imaging mode changeover occurs to the time T2 at which X-ray radioscopic imaging ends.

The time Tf5max applies to a case where the X-ray radioscopic imaging frame rate Fr=10. For example, when the X-ray radioscopic imaging frame rate Fr≥10, the time Tf5max may be fixed to 100 ms. Otherwise, when the X-ray radioscopic imaging frame rate Fr<10, the time Tf5max may be set to a small value for each frame rate Fr. As an example, a relation between the frame rate Fr, the time Tf5max, and the time Tc is illustrated in FIG. 7.

The second imaging mode start adjustment unit 109 has a table of Tf5max illustrated in FIG. 7, and calculates the time Tc based on the X-ray radioscopic imaging frame rate Fr by using formula (2). The second imaging mode start adjustment unit 109 may have a table of the time Tc already calculated by formula (2), for each X-ray radioscopic imaging frame rate Fr. Other configurations are similar to those of the first exemplary embodiment.

A fourth exemplary embodiment of the present invention will be described below. Similar to the first exemplary embodiment, the first imaging mode denotes pulsed X-ray radioscopic imaging and the second imaging mode denotes general imaging.

Figure 8:
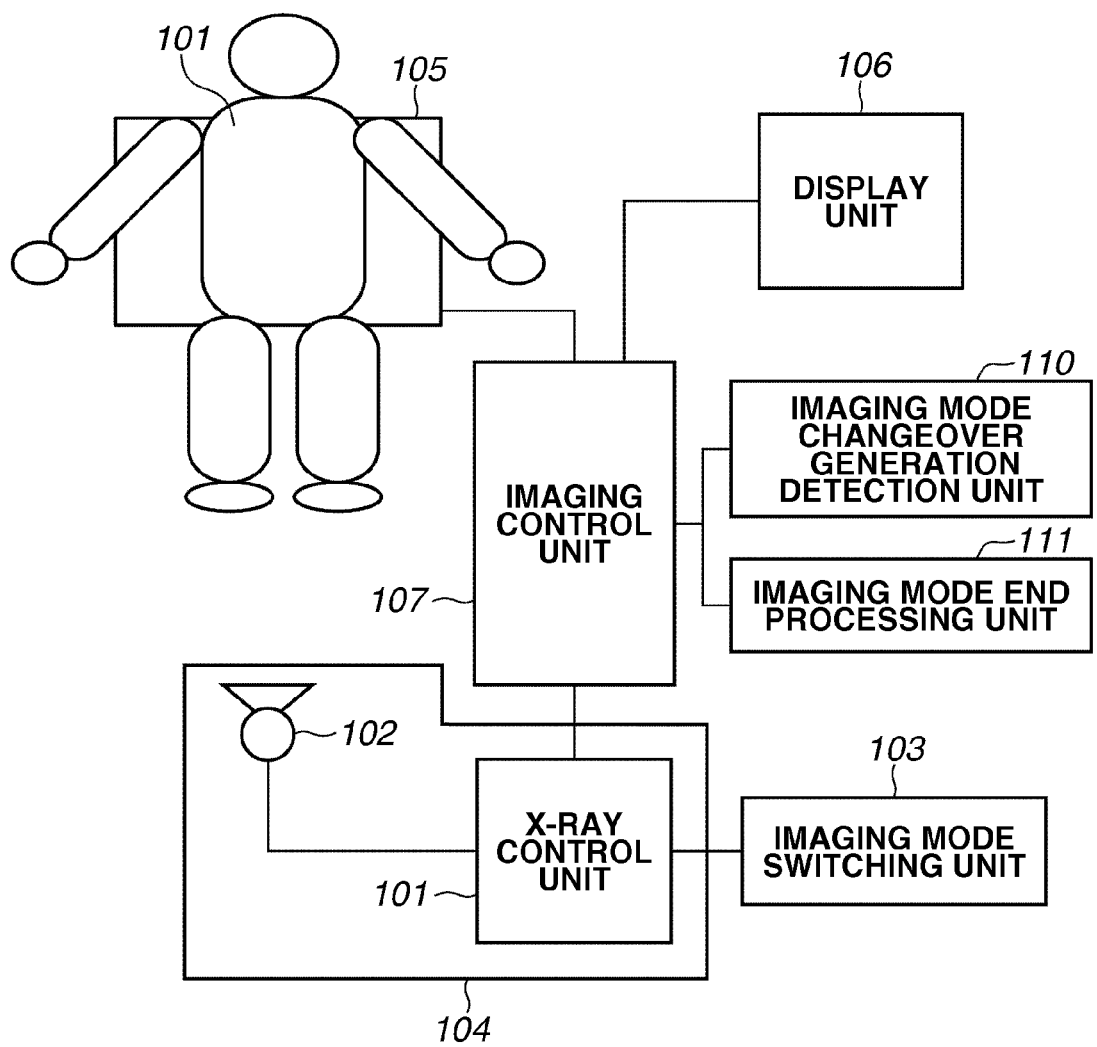
FIG. 8 is a schematic block diagram illustrating an X-ray imaging apparatus according to a fourth exemplary embodiment.

FIG. 8 is a schematic block diagram illustrating an X-ray imaging apparatus capable of performing pulsed X-ray radioscopic imaging and general imaging of the embodiment.

Unlike the X-ray imaging apparatus according to the first exemplary embodiment, instead of the first imaging mode end measurement unit 108 and the second imaging mode start adjustment unit 109, the X-ray imaging apparatus according to the fourth exemplary embodiment includes an imaging mode changeover generation detection unit 110 and an imaging mode end processing unit 111. The imaging mode changeover generation detection unit 110 detects processing to be performed when a mode changeover request is generated. The imaging mode end processing unit 111 selects a method for ending the first imaging mode according to the result of the detection by the imaging mode changeover generation detection unit 110. Other configurations are similar to those of the first exemplary embodiment.

Figure 9:
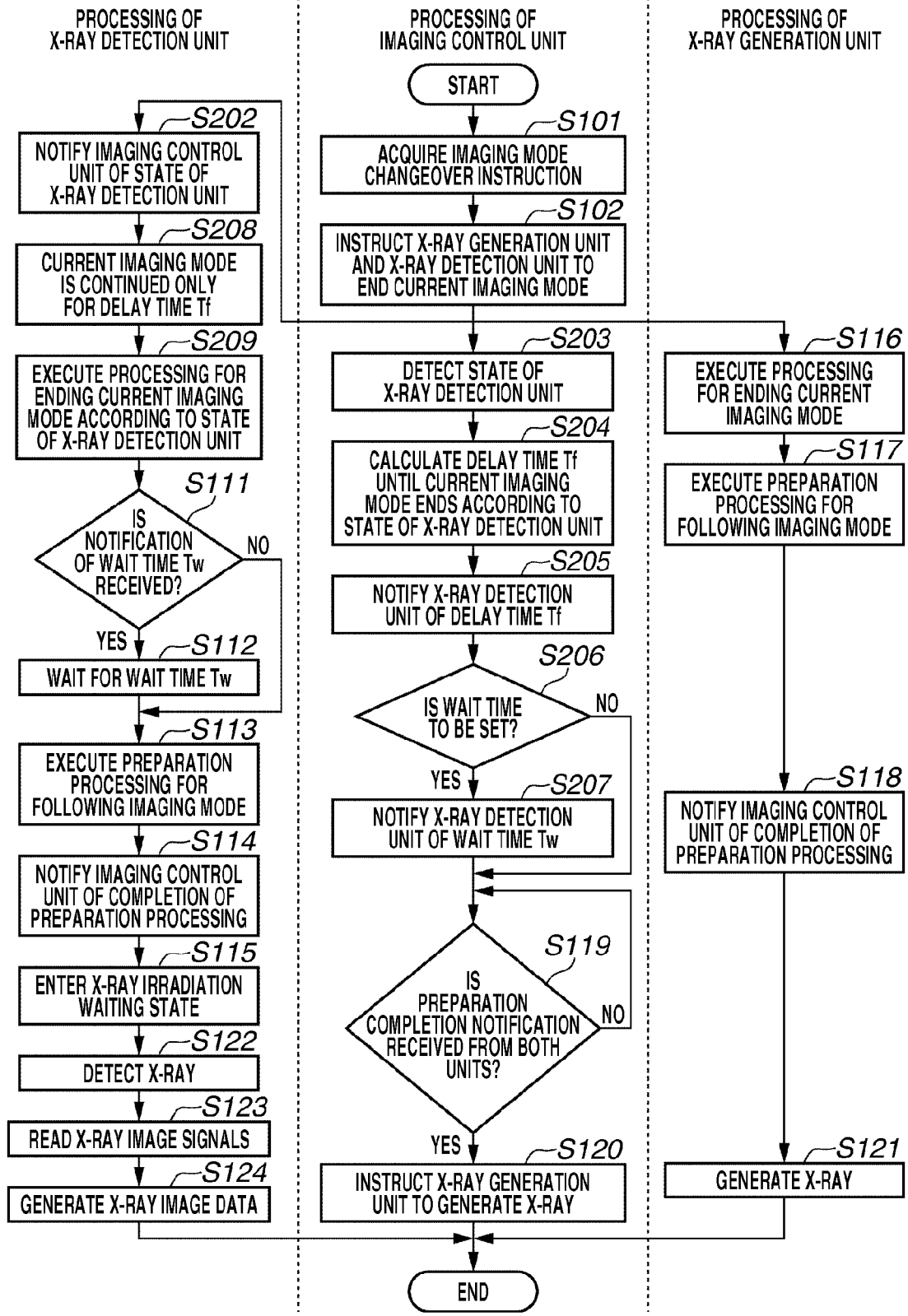
FIG. 9 is a flowchart illustrating a flow of processing performed by the X-ray imaging system according to the fourth exemplary embodiment.

A flow of processing according to the present exemplary embodiment will be described below with reference to FIG. 9. As for processing same as that described with reference to FIG. 2 in the first exemplary embodiment, redundant description will be omitted.

In step S202, the X-ray detection unit 105 notifies the imaging control unit 107 of the state of the X-ray detection unit 105 at a timing at which a mode changeover instruction is generated. Thus, in the present exemplary embodiment, instead of measuring a time since a mode changeover instruction is generated until the current imaging mode ends, the imaging control unit 107 detects the state of the X-ray imaging system when a mode changeover instruction is generated. Specifically, the imaging control unit 107 detects the operating state of the imaging system when the relevant instruction is detected.

States of the X-ray imaging system include an X-ray radiating state, as well as states of the X-ray detection unit 105, such as an electrical signal reading state, a dark current signal storing state, an X-ray image data transferring state.

In step S203, the imaging mode changeover generation detection unit 110 of the imaging control unit 107 detects the state of the X-ray detection unit 105 based on notified information and then stores the relevant information in memory. In step S204, the imaging control unit 107 determines a delay time (wait time) duration Tf until the current imaging mode ends according to the detected information. Similar to the wait time Tw according to the first to third exemplary embodiments, the delay time Tf compensates variation in the mode transition time and variation in the mode transition time of the X-ray generation unit 104, due to a difference in timing at which a mode changeover instruction is received.

In step S205, the imaging control unit 107 notifies the X-ray detection unit 105 of the delay time Tf. The relevant notification serves as a control signal for instructing the X-ray detection unit 105 to continue the current imaging mode for the delay time Tf and then ending the current imaging mode.

Thus, in the present exemplary embodiment, even if the relevant instruction is generated during one-unit imaging in the current imaging mode, the imaging system sometimes waits for a predetermined wait time and then interrupts imaging, without waiting for the end of one-unit imaging. Specifically, the imaging control unit 107 performs control for interrupting imaging in the first imaging mode. This processing enables shortening the time required for imaging mode transition to a further extent than in the first to third exemplary embodiments.

In step S206, the imaging control unit 107 determines whether a wait time is to be set. In the present exemplary embodiment, depending on situation, a wait time is not to be provided after the current imaging mode ends. Omitting the processing for providing a wait time as in the first to third exemplary embodiments enables reducing the time required for imaging mode transition. In this case, although an increase in variation in the time required for imaging mode transition can be expected, the variation is absorbed by providing the delay time Tf before the current imaging mode ends. If preventing variation in the time required for imaging mode transition is emphasized, a wait time can be provided after the current imaging mode ends.

The determination in step S206 is made based on setting information preset by a user or service person.

As another example, in a case of imaging with a frame rate smaller than a predetermined threshold value, where the time required for imaging mode transition is likely to increase, await time is not provided after the current imaging mode ends. When the time required for imaging mode transition is short, variation can be prevented by providing await time. Otherwise, when the relevant time is long, the increase in the mode transition time can be prevented without providing a wait time after the current imaging mode ends.

In step S207, the imaging control unit 107 determines the wait time Tw after the current imaging mode ends according to the detected operating state of the X-ray detection unit 105. Then, the imaging control unit 107 notifies the X-ray detection unit 105 of the wait time Tw. Specifically, the imaging control unit 107 instructs the X-ray detection unit 105 to wait for at least the wait time Tw at at least one of a timing before starting control for ending the first imaging mode and a timing before starting control for preparing for executing the second imaging mode.

Figure 11:
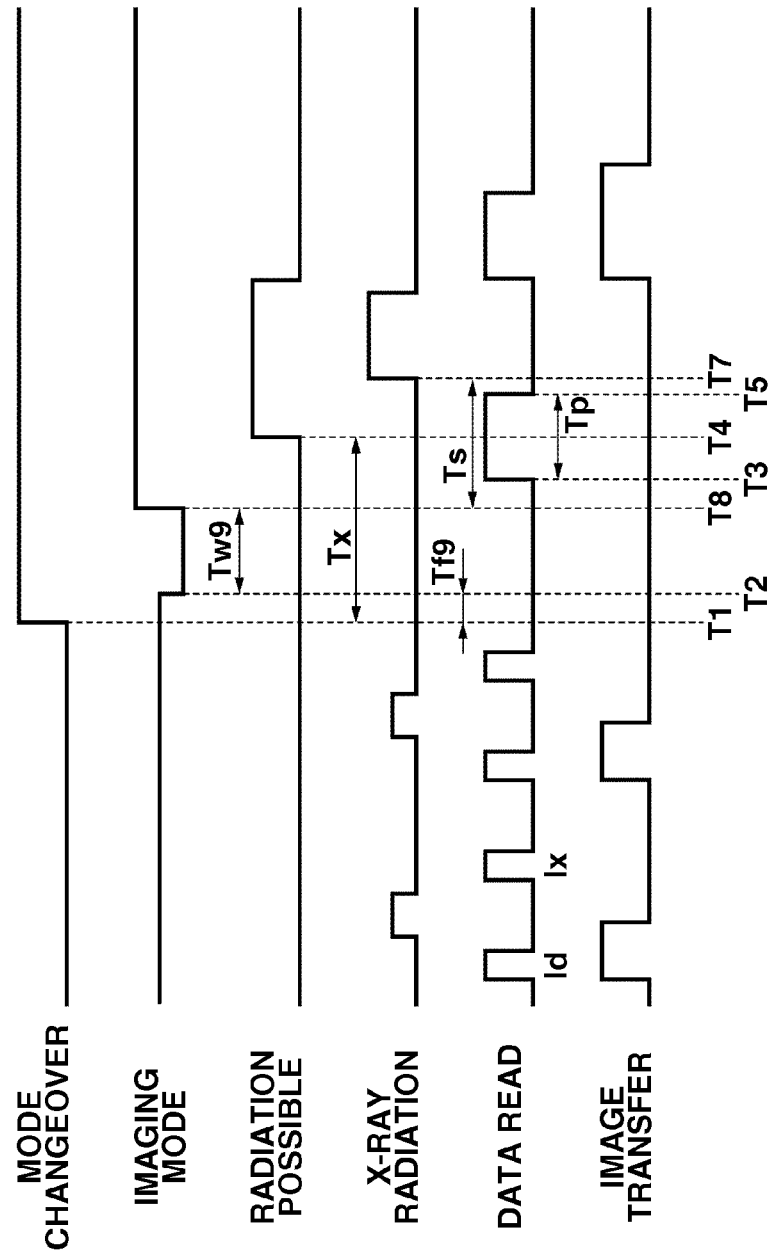
FIG. 11 is a timing chart illustrating a case where a mode changeover request for switching from pulsed X-ray radioscopic imaging to general imaging is generated during storage processing P4 when X-ray is not radiated, according to the fourth exemplary embodiment.
Figure 12:
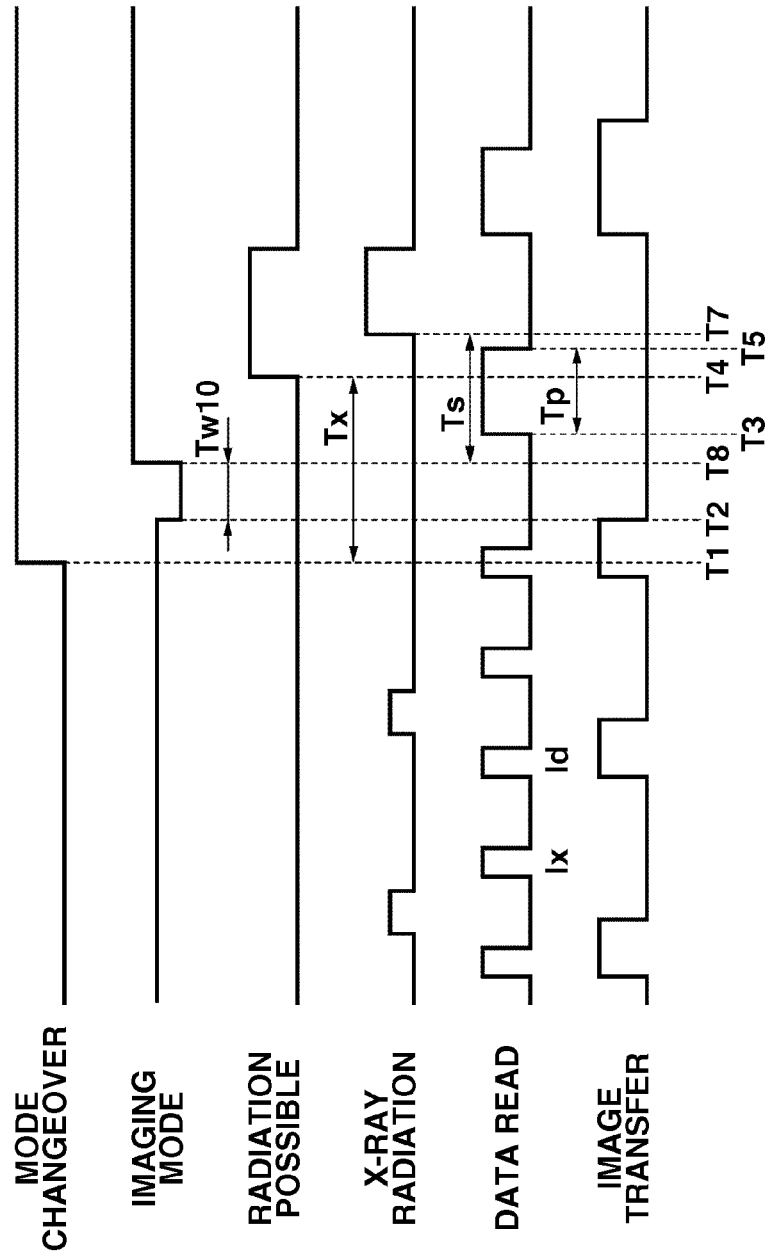
FIG. 12 is a timing chart illustrating a case where a mode changeover request for switching from pulsed X-ray radioscopic imaging to general imaging is generated during image transfer processing P1, according to the fourth exemplary embodiment.

In the meantime, in step S208, the X-ray detection unit 105 continues the current imaging mode for the delay time Tf in response to the relevant notification from the imaging control unit 107. In step S209, the X-ray detection unit 105 ends the current imaging mode. In this case, the X-ray detection unit 105 performs processing for ending the current imaging mode immediately after the relevant wait time Tw has elapsed. The imaging mode changeover generation detection unit 110 and the imaging mode end processing unit 111 will be described below with reference to timing charts illustrated in FIGS. 10, 11, and 12. The timing charts illustrated in FIGS. 10, 11, and 12 are based on a method discussed in Japanese Patent Application Laid-Open No. 3-62500.

Figure 10:
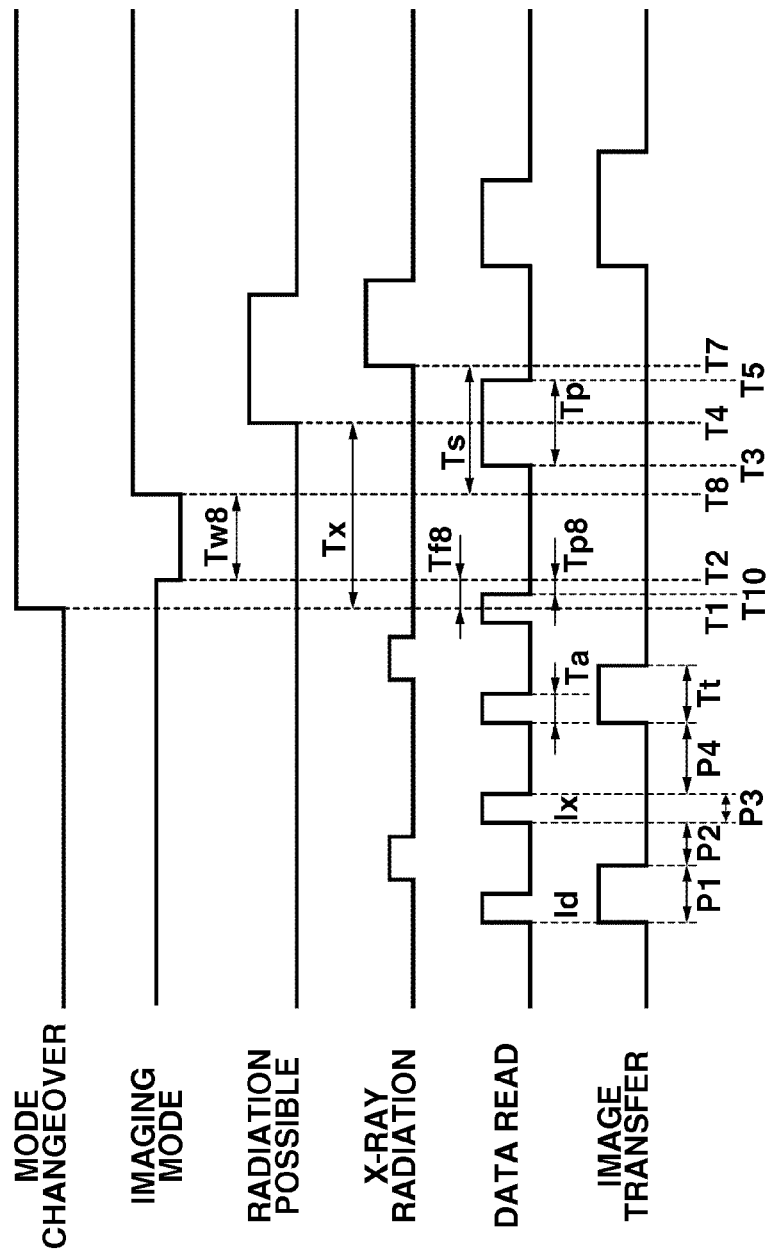
FIG. 10 is a timing chart illustrating a case where a mode changeover request for switching from pulsed X-ray radioscopic imaging to general imaging is generated, according to the fourth exemplary embodiment.

Referring to FIG. 10, a time Ta indicates an image read time during X-ray radioscopic imaging. Tt indicates an image transfer time during X-ray radioscopic imaging. At a time T10, a data read operation ends. Tp8 indicates a time since the data read operation ends until X-ray radioscopic imaging ends. Tf8 indicates a time since a mode changeover request is generated until X-ray radioscopic imaging ends. Tw8 indicates a wait time since X-ray radioscopic imaging ends until general imaging starts.

The imaging mode changeover generation detection unit 110 monitors the X-ray control unit 101 and the X-ray detection unit 105. The imaging mode changeover generation detection unit 110 divides X-ray radioscopic imaging processing into storage processing P2 for the detection elements of the X-ray detection unit 105 during X-ray radiation, storage processing P4 for the detection elements of the X-ray detection unit 105 when no X-ray radiation is performed, data read processing P3, and image transfer processing P1. The imaging control unit 107 determines the processing during which a mode changeover request is generated during X-ray radioscopic imaging. However, when both the X-ray radiation processing and the image transfer processing simultaneously occur, it is the image transfer processing P1. When both the data read processing and the image transfer processing simultaneously occur, it is the image transfer processing P1.

The imaging mode end processing unit 111 changes a method for ending the X-ray radioscopic imaging processing according to processing detected by the imaging mode changeover generation detection unit 110.

FIG. 10 illustrates a case where the imaging mode changeover generation detection unit 110 detects a mode changeover request during the data (Ix) read processing P3 during X-ray radioscopic imaging. In this case, the imaging mode changeover generation detection unit 110 notifies the imaging mode end processing unit 111 that the relevant request is detected. Then, the imaging mode end processing unit 111 reads data, performs wait processing for the time Tp8, and then ends X-ray radioscopic imaging. Then, the imaging mode end processing unit 111 performs again wait processing for the time Tw8 and then starts general imaging.

In the first to third exemplary embodiments, when a mode changeover request is generated during image (Ix) read processing, the imaging mode end processing unit 111 reads data (Ix), performs a storage operation without X-ray radiation, reads data (Id), transfers an image, and then ends X-ray radioscopic imaging. In the fourth exemplary embodiment, on the other hand, the imaging mode end processing unit 111 reads data (Ix), waits for the time Tp8, and then ends X-ray radioscopic imaging, thus remarkably shortening the time Tf8 until X-ray radioscopic imaging ends.

The wait time Tp8 is calculated by the following formula (4).

$$Tp8 = b*(Tt-Ta)(0.0 \leq b) \tag{4}$$

where Ta indicates an image read time during X-ray radioscopic imaging, Tt indicates an image transfer time during X-ray radioscopic imaging, and b indicates a decimal number satisfying the condition described in formula (4). The decimal number b will be described in detail below.

The wait time Tw8 since X-ray radioscopic imaging ends until general imaging starts is calculated by the following formula (5).

$$Tw8 = Tx - c*Ts(0.0 \leq c) \tag{5}$$

where Tx indicates a time from the time T1 at which a mode changeover request is generated to the time 14 at which the X-ray generation unit 104 becomes ready for executing general imaging, Ts indicates a time from the time T8 at which general imaging is selected to the time T7 at which the X-ray generation unit 104 starts X-ray radiation for general imaging, and c indicates a decimal number satisfying the condition described in formula (5). The decimal c will be described in detail below.

FIG. 11 illustrates a case where the imaging mode changeover generation detection unit 110 detects a mode changeover request during the storage processing P4 when X-ray radiation is not performed. In this case, the imaging mode changeover generation detection unit 110 notifies the imaging mode end processing unit 111 that the relevant request is detected. Then, the imaging mode end processing unit 111 reads data, performs wait processing for a time Tp9, and then ends X-ray radioscopic imaging. Then, the imaging mode end processing unit 111 performs again wait processing for a time Tw9 and then starts general imaging.

In the first to third exemplary embodiments, when a mode changeover request is generated during the storage processing after the data (Ix) read processing, the imaging mode end processing unit 111 reads data (Id), transfers an image, and then ends X-ray radioscopic imaging. On the other hand, when a mode changeover request is generated during the storage processing P4, the imaging mode end processing unit 111 reads data (Ix), performs wait processing for the time Tp9, and then ends X-ray radioscopic imaging, thus remarkably shortening the time Tf9 until X-ray radioscopic imaging ends. For example, the wait time Tw9 is the same time as the time Tw8 illustrated in FIG. 10.

The wait time Tp9 is calculated by the following formula (6).

$$Tp9 = b*Tt(0.0 \leq b) \tag{6}$$

where Tt indicates an image transfer time during X-ray radioscopic imaging and b indicates a decimal number satisfying the condition described in formula (6), for example, indicates the same value as in formula (4).

When the imaging mode changeover generation detection unit 110 detects a mode changeover request during the storage processing P2 for the detection elements during X-ray radiation, the imaging mode end processing unit 111 performs the almost same processing as in the case where the relevant request is generated during the storage processing P4 illustrated in FIG. 11. Specifically, when a mode changeover request is generated during the storage processing P2, the imaging mode end processing unit 111 ends X-ray radiation, waits for the time Tp9, and then ends X-ray radioscopic imaging. Subsequent processing is similar to the relevant processing described above. In this case, therefore, the time Tf9 until X-ray radioscopic imaging ends can be shortened for the same reason.

FIG. 12 illustrates a case where the imaging mode changeover generation detection unit 110 detects a mode changeover request during the image transfer processing P1. In this case, the imaging mode changeover generation detection unit 110 notifies the imaging mode end processing unit 111 that the relevant request is detected. Then, upon completion of image transfer, the imaging mode end processing unit 111 ends X-ray radioscopic imaging, performs wait processing for a time Tw10, and then starts general imaging. For example, the wait time Tw10 is the same as the time Tw8 illustrated in FIG. 10. When a mode changeover request is generated during the image transfer processing P1, a time until X-ray radioscopic imaging ends is the same as that in the first to third exemplary embodiments, and is a short time.

As described above, the imaging mode changeover generation detection unit 110 detects the processing performed when a mode changeover request is generated, and the imaging mode end processing unit 111 changes the method for ending the X-ray radioscopic imaging processing based on the result of the detection. When a mode changeover request is generated during the image transfer processing P1, the imaging mode end processing unit 111 ends X-ray radioscopic imaging when the image transfer processing ends. When a mode changeover request is generated during the storage processing P2 or P4, the imaging mode end processing unit 111 performs wait processing for the time Tp9 and then ends X-ray radioscopic imaging. When a mode changeover request is generated during the data read processing P3, the imaging mode end processing unit 111 reads data, performs wait processing for the time Tp8, and then ends X-ray radioscopic imaging.

Therefore, a time since a mode changeover request is generated until X-ray radioscopic imaging ends is shortened. Even if the X-ray radioscopic imaging frame rate Fr changes, the time since a mode changeover request is generated until X-ray radioscopic imaging ends remains unchanged.

The decimal number b in the formulas (4) and (5) will be described below. When a mode changeover request is generated during the data read processing P3, the time Tp8 changes between the time Tp8 and a time Ta+Tp8. Therefore, for example, when the decimal number b=0.5 is set in formula (4), the following formula (7) holds.

$$0.5*(Tt-Ta) \leq Tp8 \leq 0.5*(Tt+Ta) \tag{7}$$

When a mode changeover request is generated during the storage processing P2 or P4, the time Tp9 becomes the time Tp9 calculated by formula (6). Therefore, for example, when the decimal number b=0.5 is set in formula (6), the following formula (8) holds.

$$Tp9 = 0.5*Tt \tag{8}$$

When a mode changeover request is generated during the image transfer processing P1, the time Tf10 changes between 0 and the time Tt and hence the following formula (9) is given.

$$0.0 \leq Tp10 \leq Tt \qquad (9)$$

Therefore, when b=0.5 in the formulas (4) and (6) and, for example, Tt=30 ms and Ta=20 ms, an average time since an X-ray radioscopic imaging request is generated in imaging mode changeover processing until X-ray radioscopic imaging ends, is 15 ms, and a relevant maximum time is 30 ms.

The decimal number c in formula (5) will be described below. The decimal number c serves as a coefficient for preventing the number of reset operations performed before general imaging from increasing. The decimal number c in the present exemplary embodiment resembles the decimal number a described in the first exemplary embodiment. However, although, in the first exemplary embodiment, the decimal number a in formula (1) is preferably provided for each X-ray radioscopic imaging frame rate Fr, the decimal number c in formula (5) is preferably be a fixed value regardless of the X-ray radioscopic imaging frame rate Fr.

Although, in the first exemplary embodiment, variation in the X-ray radioscopic imaging frame rate Fr largely changes the time until X-ray radioscopic imaging ends, the time until X-ray radioscopic imaging ends does not depend on the X-ray radioscopic imaging frame rate Fr in the fourth exemplary embodiment.

For example, when the time Tx=400±30 ms and the time Tp=300 ms, the decimal number c=about 1.0 is desirable. Therefore, if the time Tx is known, the decimal number c is determined according to the time Tx. The imaging mode end processing unit 111 stores the determined decimal number c in memory.

Although, in the fourth exemplary embodiment, the time until X-ray radioscopic imaging ends varies depending on the timing at which a mode changeover request is generated, if the decimal number c is set to a suitable value, the variation in the time can be absorbed through the reset processing for erasing an image lag in X-ray radioscopic imaging.

In the fourth exemplary embodiment, since the offset correction discussed in Japanese Patent Application Laid-Open No. 3-62500 is used, the X-ray detection unit 105 reads charges twice for one X-ray radiation and then subtracts the data read when X-ray radiation is not performed, from the data read after X-ray radiation is performed, to generate an X-ray image. However, the processing is not limited thereto. For example, an offset image is acquired in advance, and the X-ray detection unit 105 reads charges after X-ray radiation and then subtracts the preacquired offset data from the read data to generate an X-ray image.

However, in this case, the storage processing P4 when X-ray radiation is not performed, is no longer required. Therefore, the imaging mode changeover generation detection unit 110 divides X-ray radioscopic imaging processing into storage processing P2 for the detection elements in the X-ray detection unit 105 during X-ray radiation, image read processing P3, and image transfer processing P1. Then, the imaging mode changeover generation detection unit 110 determines the processing during which a mode changeover request is generated in X-ray radioscopic imaging. Subsequent processing is similar to the relevant processing described above.

Although, in the fourth exemplary embodiment, the imaging mode switching unit 103 is connected with the X-ray control unit 101 and includes the X-ray radioscopic imaging switch and the general imaging switch, an exemplary embodiment is not limited thereto. For example, the imaging control unit 107 may include a touch panel which is operated by an operator.

Although, in the fourth exemplary embodiment, the imaging control unit 107 includes the imaging mode changeover generation detection unit 110 and the imaging mode end processing unit 111, the configuration is not limited thereto. For example, these two units may be included within the X-ray detection unit 105.

Although, in the first exemplary embodiment, the first imaging mode denotes pulsed X-ray radioscopic imaging and the second imaging mode denotes general imaging, an exemplary embodiment is not limited thereto. It is possible that the first imaging mode denotes pulsed serial imaging and the second imaging mode denotes general imaging, or that the first imaging mode denotes pulsed X-ray radioscopic imaging and the second imaging mode denotes pulsed serial imaging.

Although, in the first imaging mode, the first imaging mode denotes pulsed X-ray radioscopic imaging and the second imaging mode denotes general imaging, an exemplary embodiment is not limited thereto. Moving image capturing may denote X-ray radioscopic imaging or continuous serial imaging.

A fifth exemplary embodiment of the present invention will be described below.

In the fifth exemplary embodiment, an X-ray imaging apparatus has a similar configuration to the X-ray imaging apparatus according to the fourth exemplary embodiment, and the first imaging mode denotes pulsed X-ray radioscopic imaging and the second imaging mode denotes general imaging. However, the X-ray generation unit 104 has a long changeover time Tx for switching from X-ray radioscopic imaging to general imaging. As an example, a case where the time Tx=1000 m±200 will be described below. A time since a mode changeover request is generated until X-ray radioscopic imaging ends does not depends on the X-ray radioscopic imaging frame rate Fr, and therefore is regarded as the same as that according to the fourth exemplary embodiment.

In the fifth exemplary embodiment, the time Tx largely varies. Therefore, if the time Tx is prolonged, the X-ray generation unit 104 has not yet become ready for executing general imaging when the reset operation for erasing an image lag which occurs in X-ray radioscopic imaging is completed. In this case, the X-ray detection unit 105 performs the reset operation a number of times until the X-ray generation unit 104 becomes ready for general imaging. When the reset operation time Tp=300 ms as in the fourth exemplary embodiment, if the number of reset operations is increased by one, the time Ts since the X-ray generation unit 104 starts preparation for general imaging until general imaging is executed, is prolonged by 300 ms. To shorten the extension of the time Ts, the reset operation is preferably shortened.

Figure 13:
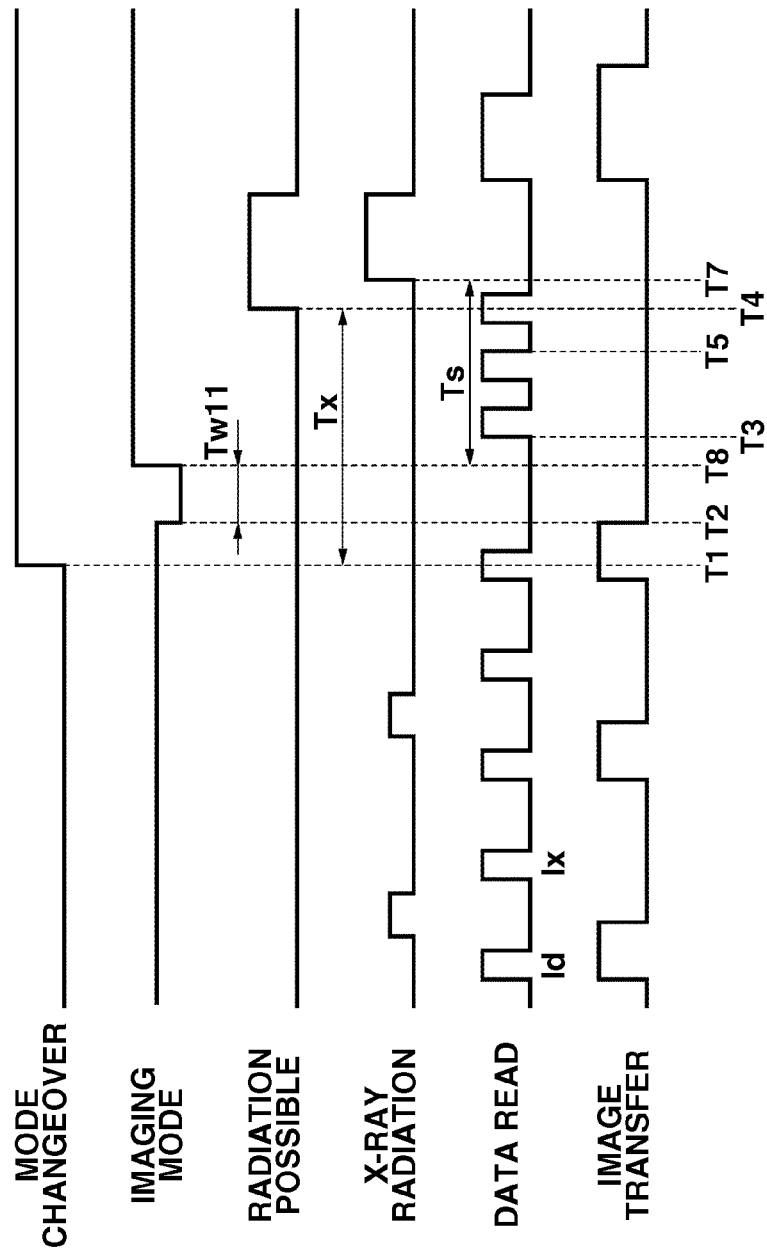
FIG. 13 is a timing chart illustrating a case where a mode changeover request for switching from pulsed X-ray radioscopic imaging to general imaging is generated, according to a fifth exemplary embodiment.

FIG. 13 is a timing chart illustrating a case where the reset operation is shortened.

Referring to FIG. 13, since the reset operation is short, it is necessary to increase the number of reset operations. However, even if the time Tx is prolonged and accordingly the number of reset operations increases, the time for switching from X-ray radioscopic imaging to general imaging is only slightly prolonged thereby.

Wait processing for a time Tw11 is performed when switching from X-ray radioscopic imaging to general imaging, the wait time Tw11 can be omitted when the processing reset operation time is short. Although, omitting the wait time Tw11 increases the number of reset operations, the time for switching from X-ray radioscopic imaging to general imaging is only slightly prolonged thereby. Other configurations are similar to those of the fourth exemplary embodiment.

A sixth exemplary embodiment of the present invention will be described below.

In the sixth exemplary embodiment, an X-ray imaging apparatus has a similar configuration to the X-ray imaging apparatus according to the fourth exemplary embodiment except the imaging mode switching unit 103. The imaging mode switching unit 103 according to the sixth exemplary embodiment has a similar configuration to the imaging mode switching unit 103 according to the third exemplary embodiment.

The X-ray generation unit 104 is similar to an X-ray generation unit discussed in Japanese Patent Application Laid-Open No. 2003-33340. In this case, the changeover time Tx of the X-ray generation unit 104 for switching from X-ray radioscopic imaging to general imaging is so short that it can be ignored. Similar to the fourth exemplary embodiment, the first imaging mode denotes pulsed X-ray radioscopic imaging and the second imaging mode denotes general imaging.

Figure 14:
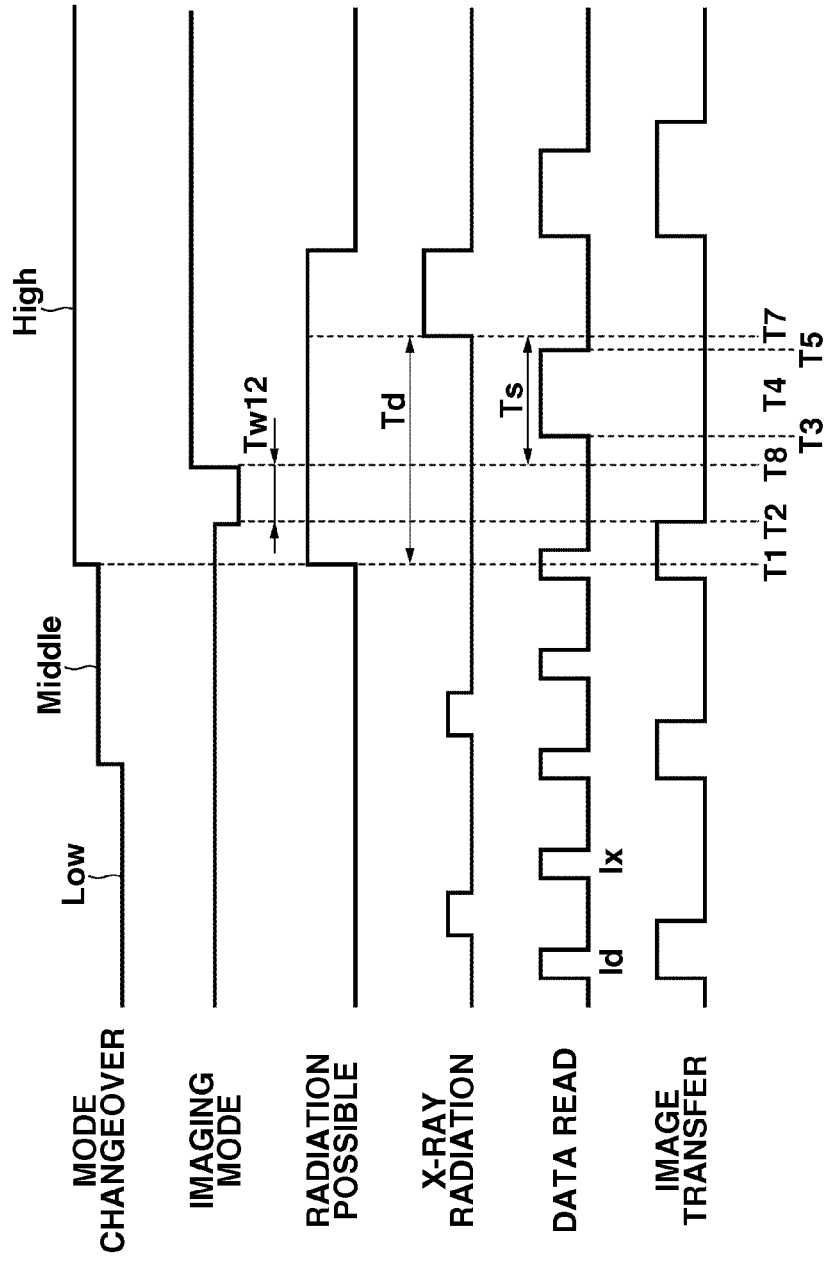
FIG. 14 is a timing chart illustrating a case where a mode changeover request for switching from pulsed X-ray radioscopic imaging to general imaging is generated, according to a sixth exemplary embodiment.

FIG. 14 is a timing chart according to the sixth exemplary embodiment.

Referring to FIG. 14, the mode changeover according to the present exemplary embodiment is similar to that according to the third exemplary embodiment, as described below. The Low level indicates a state where the X-ray generation unit 104 is performing X-ray radioscopic imaging. The Middle level indicates a state where the general imaging switch is pressed during X-ray radioscopic imaging and the X-ray generation unit 104 is performing the preparation operation for general imaging during X-ray radioscopic imaging. The High level indicates a state where the X-ray generation unit 104 has become ready for general imaging and a mode changeover request for switching from X-ray radioscopic imaging to general imaging is generated. Td indicates a time from the time T1 at which the X-ray generation unit 104 becomes ready for general imaging during X-ray radioscopic imaging to the time T7 at which it starts X-ray radiation for general imaging.

FIG. 14 illustrates a case where the imaging mode changeover generation detection unit 110 detects a mode changeover request during the image transfer processing P1. In this case, as described in the fourth exemplary embodiment, the imaging mode end processing unit 111 ends X-ray radioscopic imaging upon completion of the image transfer processing P1. Then, the imaging mode end processing unit 111 performs wait processing for a time Tw12 and then starts general imaging. The wait time Tw12 is calculated by the following formula (10).

$$Tw12 = Td - d \cdot Ts \, (0.0 \le d) \quad (10)$$

where Td indicates a time from the time T1 to the time T7, Ts indicates a time from the time T8 at which general imaging is selected, to the time T7 at which the X-ray generation unit 104 starts X-ray radiation for general imaging, and d indicates a decimal number satisfying the condition described in formula (10).

The decimal number d serves as a coefficient for preventing an increase in the number of reset operations performed before general imaging. The decimal number d in the present exemplary embodiment is similar to the decimal number c in formula (5) described in the fourth exemplary embodiment. For example, when the time Td=400 ms and the time Ts=300 ms, the decimal number c=about 1.0 is desirable. Then, the imaging mode end processing unit 111 stores the decimal number c in memory.

The sixth exemplary embodiment relates to a case where a mode changeover request is generated during the image transfer processing P1. Cases where the relevant request is generated during other processing are similar to those according to the fourth exemplary embodiment, and redundant description thereof will be omitted.

In a seventh exemplary embodiment, await time is not necessarily provided, and the reset operation is shortened as illustrated in FIGS. 5 and 13. The imaging control unit 107 performs an initialization operation (reset operation) for repeating reading of an electrical signal from the image sensor. The imaging control unit 107 includes a detection unit for detecting an imaging mode start instruction from the imaging mode switching unit 103, and an acquisition unit for acquiring an imaging mode related to the relevant instruction and a sensor state when the relevant instruction is generated. The imaging control unit 107 further includes a control unit for performing control so that the read operation repetition interval in an initialization operation at the time of transition from a predetermined imaging mode to the still image capturing mode is shorter than the relevant interval in an initialization operation at the time of transition from a non-imaging state to the still image capturing mode. The relevant control is performed based on the acquired imaging mode and the sensor state.

The present exemplary embodiment neither measures a time since a mode changeover instruction is received until the current imaging mode ends nor detects the state of the X-ray imaging system when a mode changeover instruction is received. In addition, a wait time or delay time is not necessarily required. The apparatus configuration is similar to that according to the above-described exemplary embodiments, and descriptions thereof will be omitted.

Figure 15:
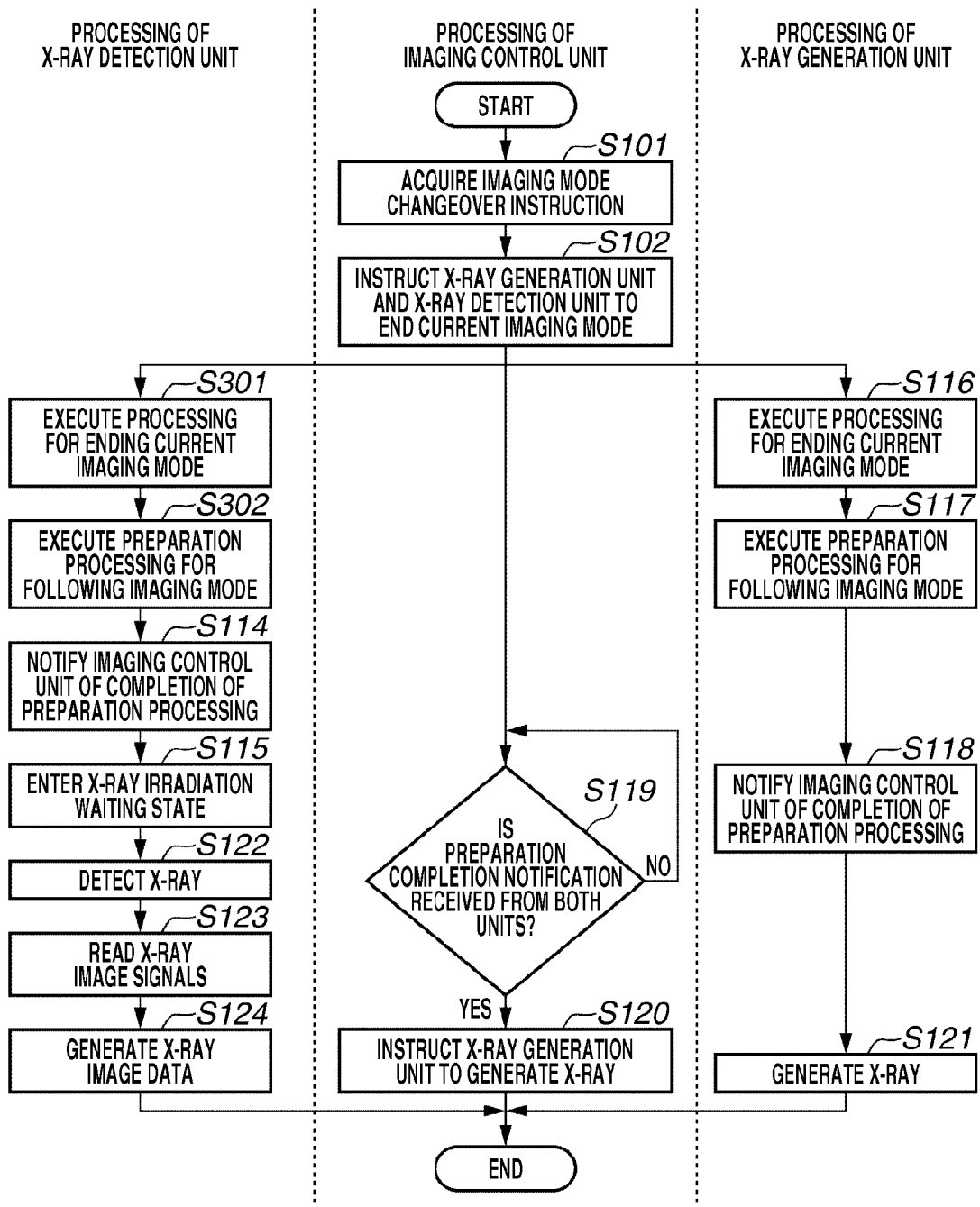
FIG. 15 is a flowchart illustrating a flow of processing performed by an X-ray imaging system according to a seventh exemplary embodiment.

A flow of processing according to the present exemplary embodiment will be described below with reference to FIG. 15. As for processing same as that described with reference to FIGS. 2 and 9, redundant description will be omitted.

In step S301, the X-ray detection unit 105 performs processing for ending the current imaging mode. Upon reception of the relevant instruction, the X-ray detection unit 105 immediately ends the current imaging mode. Specifically, when the relevant instruction is generated at a predetermined timing, in step S302 (in which a wait time is set to 0), the X-ray detection unit 105 performs processing for ending the current imaging mode and then the preparation processing for the following imaging mode.

In the present exemplary embodiment, the preparation processing for the following imaging mode is the initialization operation (reset operation) for repeating electrical signal elimination at short intervals. Therefore, even if the generation unit 104 becomes ready during charge elimination, an initialization operation for one unit is performed in a short time.

Therefore, unless variation in the mode transition time of the generation unit 104 is taken into consideration, variation in the time required for imaging mode transition as the entire system can be reduced even without providing a wait time. This means that, if charge elimination for one frame takes a long time, completing charge elimination for up to the last frame takes a remarkably long time even if the generation unit 104 becomes ready during charge elimination for one frame. Accordingly, it is obvious that the time required for imaging mode transition can be varied by the time consumed for charge elimination.

In step S301, if there is variation in the mode transition time of the generation unit 104, the X-ray detection unit 105 provides, in consideration of variation, a predetermined delay time or wait time before or after the current imaging mode ends, or after the preparation operation ends. This enables absorbing variation in the mode transition time of the generation unit 104.

Figure 16:
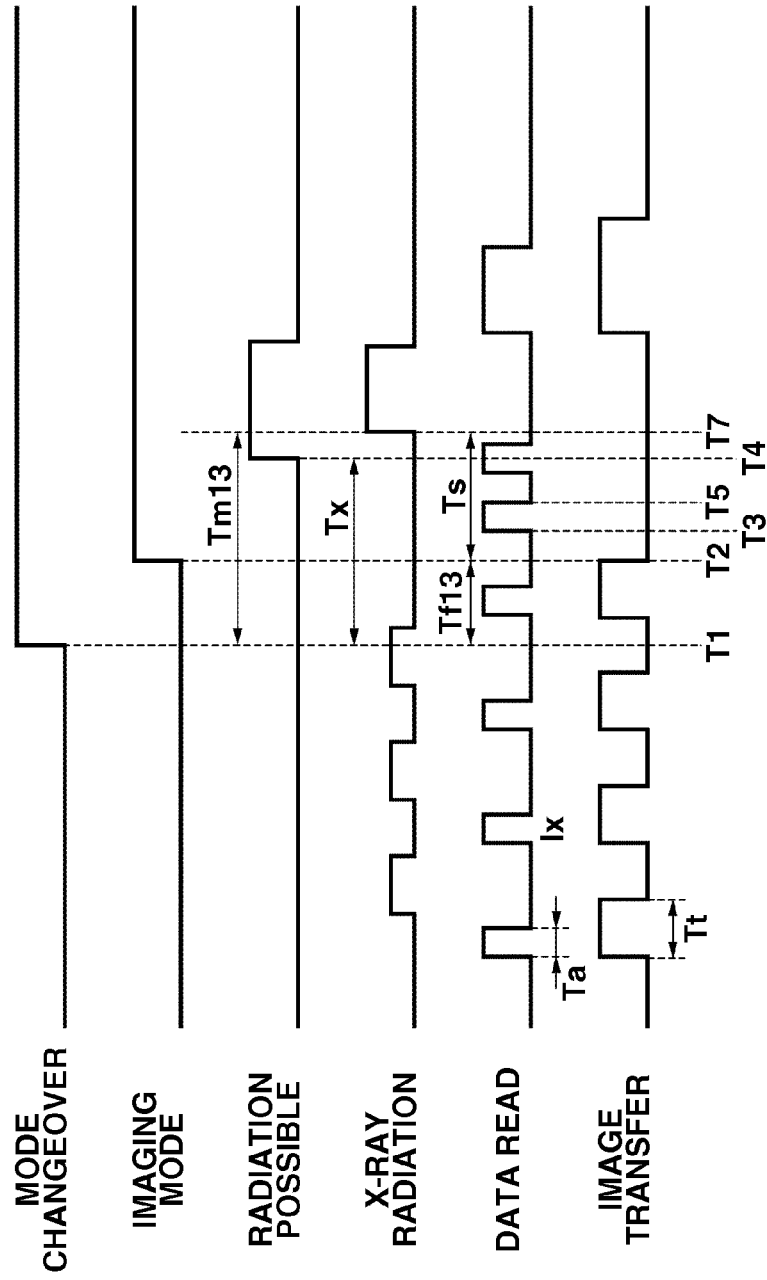
FIG. 16 is a timing chart illustrating a case where a mode changeover request for switching from pulsed X-ray radioscopic imaging to general imaging is generated, according to the seventh exemplary embodiment.

FIG. 16 is an example of a timing chart illustrating a case where an imaging mode changeover from pulsed X-ray radioscopic imaging to general imaging occurs. In this example, the X-ray detection unit 105 reads charges once for one X-ray radiation to perform offset correction for X-ray radioscopic imaging and general imaging.

Referring to FIG. 16, each signal will be described below. "MODE CHANGEOVER" indicates that a mode changeover request for switching from X-ray radioscopic imaging to general imaging is generated when a transition from the Low to High level occurs. "IMAGING MODE" indicates X-ray radioscopic imaging at the Low level and the High level indicates general imaging. "RADIATION POSSIBLE" indicates that the X-ray generation unit 104 cannot execute general imaging at the Low level and the High level indicates that it can execute general imaging. "X-RAY RADIATION" indicates that the X-ray generation unit 104 is performing X-ray radiation at the High level. "DATA READ" indicates that the X-ray detection unit 105 is reading charges from the X-ray detection elements at the High level. "IMAGE TRANSFER", indicates that the X-ray detection unit 105 is transferring an X-ray image to the imaging control unit 107 at the High level.

Generally, during X-ray radioscopic imaging, the data read time Ta is about 20 ms and the image transfer time Tt is about 30 ms. As described above, an X-ray image can be obtained by subtracting the data acquired in advance without X-ray radiation from the data (Ix) read immediately after X-ray radiation.

At the time T1, for example, the operator presses the general imaging switch during pulsed X-ray radioscopic imaging (selected by the operator by pressing the X-ray radioscopic imaging switch), and a mode changeover request for switching to general imaging is generated. When a mode changeover request is generated, the X-ray generation unit 104 starts preparation for general imaging and, at the same time, notifies the imaging control unit 107 that an changeover request for switching to general imaging is generated. When the imaging control unit 107 is notified that a mode changeover request for switching to general imaging is generated during X-ray radioscopic imaging, it instructs the X-ray detection unit 105 to end X-ray radioscopic imaging.

At the time T2, the X-ray detection unit 105 ends X-ray radioscopic imaging and general imaging is selected because a mode changeover from X-ray radioscopic imaging to the general imaging is requested at the time T1. When the X-ray detection unit 105 reads an X-ray image last captured in X-ray radioscopic imaging and then transfers the read image to the imaging control unit 107, X-ray radioscopic imaging ends. Tf13 indicates a time from the time T1 at which a mode changeover request is generated to the time T2, i.e., a time since a mode changeover request is generated until X-ray radioscopic imaging ends.

At the time T3, after general imaging is selected, the X-ray generation unit 104 starts the preparation operation for executing general imaging. Referring to FIG. 16, the X-ray detection unit 105 performs the reset operation once, and the processing time Tp is about 300 ms. During a time from the time T2 to the time T3, for example, the X-ray detection unit 105 performs processing for switching the sensitivity. This time is very short in comparison with the mode changeover time.

At the time T4, the X-ray generation unit 104 has become ready for executing general imaging. Tx indicates a time from the time T1 at which a mode changeover request is generated to the time T4. When the X-ray generation unit 104 has become ready for general imaging, it notifies the imaging control unit 107 that the X-ray generation unit 104 has become ready for general imaging. Referring to FIG. 16, as discussed in Japanese Patent Application Laid-Open No. 2000-292598, the X-ray generation unit 104 shortens a rising time for heating the filament for general imaging when switching from X-ray radioscopic imaging to general imaging.

At the time T5, the X-ray detection unit 105 ends the processing for erasing an image lag which occurs in the X-ray radioscopic imaging mode and then becomes ready for general imaging. When the X-ray detection unit 105 has become ready for general imaging, it notifies the imaging control unit 107 that the X-ray detection unit 105 has become ready for general imaging.

At a time T7, the X-ray generation unit 104 and the X-ray detection unit 105 have become ready for general imaging, and the X-ray generation unit 104 starts X-ray radiation for general imaging. The imaging control unit 107 outputs, for example, an X-ray radiation enabling signal for general imaging, to the X-ray generation unit 104. Upon reception of the signal, the X-ray generation unit 104 starts X-ray radiation for general imaging. A time from the time T5 at which the X-ray detection unit 105 becomes ready for executing general imaging to the time T7 at which the X-ray generation unit 104 starts X-ray radiation is very short in comparison with the mode changeover time.

Ts indicates a time from the time T2 at which general imaging is selected to the time T7 at which the X-ray generation unit 104 starts X-ray radiation for general imaging. When the reset operation is performed once, the time Ts is almost the same as the time Tp.

Tm13 indicates a time from the time T1 at which a mode changeover request is generated to the time T7 at which the X-ray generation unit 104 performs X-ray radiation for general imaging. Subsequent processing for general imaging is as described in the above-described exemplary embodiments.

FIG. 17 illustrates a case where an imaging mode changeover from pulsed X-ray radioscopic imaging to general imaging occurs at a different timing from that illustrated in FIG. 16. FIG. 17 uses the same symbols as those used in FIG. 16, and redundant description thereof will be omitted. Only newly added times Tf14 and Tm14 will be described below. Referring to FIG. 17, Tf14 indicates a time since a mode changeover request is generated until X-ray radioscopic imaging ends, Tm14 indicates a time since a mode changeover request is generated until X-ray radiation for general imaging starts. Referring to FIGS. 16 and 17, the time Tf14 is longer than the time Tf13, and the time Is since general imaging is selected until X-ray radiation for general imaging starts, is almost the same in both FIGS. 16 and 17. Therefore, the time Tm14 is longer than the time Tm13.

When timing changes at which a mode changeover request for switching from X-ray radioscopic imaging to general imaging is generated, the mode changeover time for switching from X-ray radioscopic imaging to general imaging changes. However, in the initialization operation at the time of transition from the X-ray radioscopic imaging mode to the still image capturing mode, the imaging control unit 107 performs control with a shorter repetition interval of read operation and with a greater number of repetitions than those in the initialization operation at the time of transition from a non-imaging state to the still image capturing mode. This control prevents variation in the mode changeover time.

FIG. 18 illustrates a case where an imaging mode changeover from pulsed X-ray radioscopic imaging to general imaging occurs at a different timing from that illustrated in FIGS. 16 and 17. Referring to FIG. 18, the frame rate is higher than that in FIGS. 16 and 17, and is determined by the interval of pulsed X-ray radiation. FIG. 18 uses the same symbols as those used in FIG. 16, and redundant description thereof will be omitted. Only newly added times Tf15, Ts15, and Tm15, and a time T6 will be described below.

Referring to FIG. 18, Tf15 indicates a time since a mode changeover request is generated until X-ray radioscopic imaging ends, and Tf15 is shorter than the time Tf13 illustrated in FIG. 16. This means that the time since a mode changeover request is generated until X-ray radioscopic imaging ends is shorter than that in FIG. 16. Referring to FIG. 18, at the time T5, the X-ray detection unit 105 completes the reset operation and the X-ray generation unit 104 has not yet become ready for executing general imaging. In this case, since the X-ray generation unit 104 is not capable of X-ray radiation, the imaging control unit 107 instructs the X-ray detection unit 105 to perform the reset operation again.

At the time T6, the X-ray detection unit 105 completes the second reset operation and the X-ray generation unit 104 has become ready for general imaging. At the time T7, the X-ray generation unit 104 starts X-ray radiation for general imaging.

Ts15 indicates a time from the time T2 to the time T7. Since the X-ray detection unit 105 performs the second reset operation immediately after the first reset operation ends, the time Ts15 is about 600 ms which is about twice the time Tp.

Tm15 indicates a time since a mode changeover request is generated until X-ray radiation for general imaging starts.

The time Tf15 since a mode changeover request is generated until X-ray radioscopic imaging ends is shorter than the time Tf13. However, the time Ts15 since general imaging is selected until X-ray radiation for general imaging starts is longer than the time Ts illustrated in FIG. 16. As a result, if a mode changeover request for switching from X-ray radioscopic imaging to general imaging is generated at a different timing, the mode changeover time Tm15 for switching from X-ray radioscopic imaging to general imaging changes compared with the time Tm13. For the same reason, variation in the frame rate during pulsed X-ray radioscopic imaging changes the mode changeover time for switching from pulsed X-ray radioscopic imaging to general imaging.

FIGS. 19, 20, and 21 are examples of timing charts illustrating cases where an imaging mode changeover from pulsed X-ray radioscopic imaging to general imaging occurs. In these examples, offset correction for X-ray radioscopic imaging is based on the method discussed in Japanese Patent Application Laid-Open No. 3-62500, and the X-ray detection unit 105 reads charges twice for one X-ray radiation. With offset correction for general imaging, an X-ray image is acquired by subtracting general imaging data acquired in advance without X-ray radiation from the data read immediately after X-ray radiation.

FIGS. 19, 20, and 21 use the same symbols as those used in FIG. 16, and redundant description thereof will be omitted. Only newly added symbols will be described below.

Referring to FIG. 19, Tf16 indicates a time since X-ray radioscopic data (Id) is read when X-ray radiation is not carried out and a mode changeover request is generated, until X-ray radioscopic imaging ends. Referring to FIG. 20, that time corresponds to Tf17. Referring to FIG. 21, that time corresponds to Tf18. Referring to FIG. 19, Tm16 indicates a time since a mode changeover request is generated until X-ray radiation for general imaging starts. Referring to FIG. 20, that time corresponds to Tm17. Referring to FIG. 21, Tm18 corresponds to the relevant time.

Referring to FIG. 19, a mode changeover request is generated at the time T1 during the data (Ix) read processing after X-ray radiation. Referring to FIG. 20, a mode changeover request is generated during the storage processing when X-ray radiation is not carried out after the data read (Ix) operation after X-ray radiation. Referring to FIG. 21, a mode changeover request is generated both during the data read (Id) operation when X-ray radiation is not carried out and during image transfer from the X-ray detection unit 105 to the imaging control unit 107.

For example, when the X-ray radioscopic imaging frame rate Fr=10, Tf16>Tf17>Tf18, and Tm18>Tm16>Tm17, as can be seen from FIGS. 19, 20, and 21. Even when offset correction discussed in Japanese Patent Application Laid-Open No. 3-62500 is performed, if a mode changeover request for switching from X-ray radioscopic imaging to general imaging is generated at a different timing, the mode changeover time for switching from X-ray radioscopic imaging to general imaging varies.

Further, in the initialization operation at the time of specific mode transition processing, the imaging control unit 107 can perform control based on the imaging mode acquired such that the repetition interval of read operation is shorter than that in the initialization operation at the time of transition from a non-imaging state to the still image capturing mode. The initialization operation at the time of specific mode transition processing includes the initialization operation at the time of transition from a predetermined imaging mode to the still image capturing mode, and the initialization operation at the time of transition from a predetermined imaging mode to the moving image capturing mode.

In consideration of combinations of the first to six exemplary embodiments, the present invention can be embodied in diverse forms. As discussed in the second exemplary embodiment with reference to FIG. 5, after completion of a predetermined imaging mode and before the initialization operation at the time of mode transition to the still image capturing mode, the imaging control unit 107 waits at least for a specific wait time and then can perform control for executing an initialization operation. Further, the imaging control unit 107 determines the specific wait time according to the time since a mode changeover instruction is generated until the predetermined imaging mode ends.

As discussed in the fifth exemplary embodiment with reference in FIG. 13, the delay time Tf may be provided before the current imaging mode ends. As discussed in the first to sixth exemplary embodiments, the wait time Tw may be provided after the current imaging mode ends. In this case, at the time of mode transition from a predetermined imaging mode to the still image capturing mode, the imaging control unit 107 waits for at least a specific wait time after acquiring a mode changeover instruction and then performs control for executing the initialization operation. Further, the imaging control unit 107 interrupts one-unit imaging in the predetermined imaging mode when a mode changeover instruction is generated, in response to the relevant instruction.

In addition, similar to the fourth to sixth exemplary embodiments, by providing a selection unit for determining whether wait processing is to be performed based on setting information, it is possible to select preventing variation in the mode transition time or reducing the mode transition time to which priority is given.

In addition, similar to the first to sixth exemplary embodiments, if the imaging control unit 107 changes the wait time according to the frame rate in the above-described moving image capturing mode, procedures for setting the wait time can be reduced. According to the setting information, the imaging control unit 107 selects the timing of performing the initialization operation, i.e., determining whether the operation is performed after interruption of one-unit imaging in a predetermined imaging mode when a mode changeover instruction is generated, in response to the relevant instruction, or after completion of the relevant one-unit imaging.

In an eighth exemplary embodiment, a selection unit for selecting at least one of a plurality of mode transition processing is provided. One of the plurality of mode transition processing is the first mode transition processing in which wait processing is performed after X-ray radioscopic imaging ends, as described in the first to sixth exemplary embodiments. Another mode transition processing is the second mode transition processing in which wait processing is performed before X-ray radioscopic imaging ends, as described in the fourth to sixth exemplary embodiments. Still another mode transition processing is the third mode transition processing in which a short reset operation is performed, as described in the seventh exemplary embodiment.

Although the selection unit is implemented as one function of the imaging control unit 107, it may be implemented as a unit different from the imaging control unit 107. The X-ray imaging system according to the present exemplary embodiment is similar to that according to the above-described exemplary embodiments, and redundant description thereof will be omitted.

A flow of processing according to the present exemplary embodiment will be described below with reference to FIG. 22. In this processing, for example, moving image capturing (first imaging mode) is executed at a timing set in the X-ray imaging system. When changing the frame rate during imaging, the imaging control unit 107 performs processing in step S401 and subsequent steps each time the frame rate is changed.

In step S401, the imaging control unit 107 acquires a frame rate setting value related to the moving image capturing. In step S402, the imaging control unit 107 acquires the time (preparation time) required for the mode transition processing of the X-ray generation unit 104. In this step, the imaging control unit 107 acquires an average value and nominal value of the mode transition time from memory. In step S403, the imaging control unit 107 acquires setting information about the mode transition processing set in advance by the user.

In step S404, the selection unit of the imaging control unit 107 determines whether variation in the preparation time of the X-ray generation unit 104 is smaller than a threshold value. When the selection unit determines that variation in the preparation time of the X-ray generation unit 104 is smaller than the threshold value (YES in step S404), the selection unit determines that a delay time or wait time for compensating variation is required, and the processing proceeds to step S405.

In step S405, the selection unit further determines whether the frame rate is smaller than a threshold value or predetermined setting information is present. When the section unit determines that the frame rate is smaller than the threshold value or the predetermined setting information is present (YES in step S405), the selection unit determines that variation in mode transition is large as the entire system, and the processing proceeds to step S406. In step S406, the selection unit sets the mode transition processing as first mode transition processing.

The first mode transition processing provides the wait time Tw after the current imaging mode ends, as described in the first to sixth exemplary embodiments. The wait time Tw may be set through timing measurement as in the first to third exemplary embodiments or through state detection as in the fourth to sixth exemplary embodiments. Thus, variation in imaging mode transition can be compensated.

According to the user-set information, the selection unit can determine whether the wait time Tw is to be set through timing measurement as in the first to third exemplary embodiments or through state detecting as in the fourth to sixth exemplary embodiments. In this case, in the first to third exemplary embodiments, the imaging control unit 107 can acquire an X-ray image corresponding to X-ray irradiation for the last frame in the current imaging mode and then display the image on the display unit 106. Based on state detection in the fourth to sixth exemplary embodiments, it is possible to interrupt one-unit imaging in the current imaging mode to enable mode transition, thus shortening the mode transition time.

Otherwise, when the selection unit determines that the frame rate is comparatively high or the predetermined setting information is present (NO in step S405), then in step S407, the selection unit sets the mode transition processing as second mode transition processing. In the second the mode transition processing, as discussed in the fourth to sixth exemplary embodiments, the imaging control unit 107 provides the delay time Tf before the current imaging mode ends to interrupt the imaging mode. Thus, the imaging mode transition time can be reduced and its variation can be suppressed.

Otherwise, when the selection unit determines that variation in the preparation time of the X-ray generation unit 104 is small (NO in step S404), the selection unit determines that the wait time required for mode transition is short, and the processing proceeds to step S408.

In step S408, the selection unit sets the mode transition processing as third mode transition processing. In the third the mode transition processing, as discussed in the seventh exemplary embodiment, the imaging control unit 107 performs a short-interval reset operation (initialization operation). Thus, the initialization time can be shortened and variation in the mode transition time resulting from the repetition of the initialization operation by the X-ray detection unit 105 can be suppressed.

Although, in the present exemplary embodiment, any one of three different mode transition processing is selected, two or more types of processing may be selected based on setting information because the three mode transition processing are not exclusive. Further, the selection unit may select one of two modes out of the three mode transition processing described in the exemplary embodiments. Specifically, the selection unit selects execution of at least one of the first and second transition modes.

The first transition mode is a transition mode in which the first imaging mode is ended in response to an instruction and a wait time is provided according to the time since the relevant instruction is generated until the first imaging mode ends. The second transition mode is a transition mode in which the first imaging mode is ended after a wait time according to the operating state of the above-described imaging system elapses when the relevant instruction is generated.

As described above, if the timing at which an imaging mode changeover from pulsed X-ray radioscopic imaging to general imaging occurs, the frame rate during pulsed X-ray radioscopic imaging, or the time required for an imaging mode changeover of the X-ray generation unit 104 varies, the mode changeover time for switching from pulsed X-ray radioscopic imaging to general imaging varies. Therefore, there has been a problem that large variation in the mode changeover time prevents the user from performing general imaging at a desired timing. If general imaging cannot be executed at a timing desired by the operator, the operator needs to perform the same imaging operation again. In this case, the X-ray dosage radiated to the subject increases.

For example, suppose that any one of pulsed X-ray radioscopic imaging, continuous X-ray radioscopic imaging, pulsed serial imaging, and continuous serial imaging is the first imaging mode, and that any one of general imaging, pulsed serial imaging, and continuous serial imaging is the second imaging mode. In this case, when an imaging mode changeover from the first imaging mode to the second imaging mode occurs, variation in the timing of an imaging mode changeover or the frame rate causes large variation in the mode changeover time for switching from the first imaging mode to the second imaging mode. Therefore, there has been a problem that the second imaging mode cannot be executed at a timing desired by the operator.

In the above-described exemplary embodiments, when an imaging mode changeover from the second imaging mode to the first imaging mode occurs, the first imaging mode end measurement unit 108 measures the time since an imaging mode changeover occurs until the first imaging mode ends. Then, the first imaging mode end measurement unit 108 adjusts the time until the second imaging mode is selected based on the measured time. Thus, variation in the time required for an imaging mode changeover can be shortened and the second imaging mode can be executed at a timing desired by the operator.

A timing chart for performing general imaging is illustrated in FIG. 23.

Referring to FIG. 23, GENERAL IMAGING REQUEST indicates the state of the general imaging switch. The Low level indicates that the general imaging switch is not pressed, and the High level indicates that it is pressed. The Low level in RADIATION POSSIBLE indicates that the X-ray generation unit 104 is not ready for performing general imaging and the High level indicates that it is ready for performing general imaging. The High level in X-RAY RADIATION indicates that the X-ray generation unit 104 is radiating the X-ray. The High level in DATA READ indicates that the X-ray detection unit 105 is reading charges from the X-ray detection elements. The High level in IMAGE TRANSFER indicates that the X-ray detection unit 105 is transferring an X-ray image to the imaging control unit 107.

Generally, when GENERAL IMAGING REQUEST is at the Low level, the X-ray detection unit 105 periodically performs the reset operation for the plane detector. The X-ray detection unit 105 performs the reset operation of the X-ray detection elements row by row, as discussed in Japanese Patent Application Laid-Open No. 2009-272673. Since the reset operation is almost the same as the video data read operation, DATA READ is set to High. However, an image read by the reset operation is discarded without being transferred.

Referring to FIG. 23, at a time T20, the general imaging switch is pressed and an imaging request is generated. When GENERAL IMAGING REQUEST is set to High, the X-ray generation unit 104 starts the preparation for X-ray radiation. Tx indicates a time duration since an imaging request is generated until the X-ray generation unit 104 becomes ready for X-ray radiation. At a time T24, the X-ray generation unit 104 becomes ready for X-ray radiation.

At the time T20, the plane detector starts the preparation operation for executing general imaging. The preparation operation for general imaging is an operation for resetting the plane detector, and is almost the same as the still image data read operation.

This reset operation has an effect of reducing the offset value when an X-ray image is captured, and is repeated till the time T24. Tp indicates the reset operating time duration for general imaging. At a time T21, the first preparation operation is completed, At a time T22, the second preparation operation is completed. At a time T23, the third preparation operation is completed.

At a time T25, the X-ray imaging apparatus becomes ready for X-ray radiation, the third reset operation for the plane detector is completed, the plane detector becomes ready for imaging, and the X-ray generation unit 104 starts X-ray radiation for general imaging. Ts indicates a time duration since an imaging request is generated until the X-ray generation unit 104 starts X-ray radiation for general imaging. Upon completion of X-ray radiation, the X-ray detection unit 105 reads charges of the X-ray detection elements and performs offset correction, and then transmits the read image to the imaging control unit 107.

The above-described exemplary embodiments are to be considered as illustrative in embodying the present invention, and does not restrict the scope of the present invention. The present invention may be embodied in diverse forms without departing from the technical concepts or essential characteristics thereof.

For example, it is presumed that an X-ray imaging apparatus includes the X-ray generation unit 104 for radiating the X-ray to a subject, the X-ray detection unit 105 having a plurality of detection elements for detecting the X-ray penetrating the subject and storing charges, an X-ray image generation unit for sequentially reading the charges stored in the detection elements to generate an X-ray image, and a transfer unit for transferring the X-ray image generated by the X-ray image generation unit to an apparatus control unit, wherein the apparatus control unit includes a display unit for displaying the received X-ray image.

The X-ray imaging apparatus includes an imaging unit having a first imaging mode and a second imaging mode, and the imaging mode switching unit 103 for switching from the first imaging mode to the second imaging mode. The X-ray imaging apparatus further includes the first imaging mode end measurement unit 108 for measuring, when an imaging mode changeover occurs, the time Tf until the first imaging mode ends. The X-ray imaging apparatus further includes the second imaging mode start adjustment unit 109 for adjusting the wait time Tw until the second imaging mode is selected based on the measured time Tf.

The first imaging mode is any one of pulsed X-ray radioscopic imaging, continuous X-ray radioscopic imaging, pulsed serial imaging, and continuous serial imaging. The second imaging mode is any one of general imaging, pulsed serial imaging, and continuous serial imaging. The imaging mode switching unit 103 determines that an imaging mode changeover from the first imaging mode to the second imaging mode has occurred when a mode changeover request is generated in the first imaging mode. The second imaging mode start adjustment unit 109 stores the time Tx from the first imaging mode until the X-ray generation unit 104 becomes ready for X-ray radiation in the second imaging mode.

The second imaging mode start adjustment unit 109 includes a unit for setting the value of the time Tx. The second imaging mode start adjustment unit 109 provides wait processing so that $Tw=Tx-Tf \times a \ast Ts$ ($a \leq 1.0$) is satisfied, where Tf indicates a measurement time, Tx indicates a time for enabling X-ray radiation, Ts indicates a preparation time for executing the second imaging mode, and Tw indicates a wait time for adjusting the changeover time for switching from the first imaging mode to the second imaging mode.

The second imaging mode start adjustment unit 109 has the decimal number a for each frame rate of the first imaging mode. When a mode changeover request is generated in the first imaging mode, the X-ray generation unit 104 prepares for the second imaging mode in the first imaging mode. When the X-ray generation unit 104 has become ready for imaging in the second imaging mode, the imaging mode switching unit 103 determines that a mode changeover has occurred.

The second imaging mode start adjustment unit 109 provides the wait processing so that Tw=Tc−Tf−Ts is satisfied, where Tc indicates a time during which the X-ray generation unit 104 changes from the first imaging mode to the second imaging mode, Ts indicates a preparation time for executing the second imaging mode, and Tw indicates a wait time for adjusting the changeover time for switching from the first imaging mode to the second imaging mode. The second imaging mode start adjustment unit 109 has the time Tc for each frame rate of the first imaging mode.

During the preparation processing for switching from the first imaging mode to the second imaging mode, the imaging mode switching unit 103 performs at least once the processing for erasing an image lag in the X-ray detection unit 105 which occurs in the first imaging mode. The imaging mode switching unit 103 performs the processing for erasing an image lag at the same time as the time of reading charges in the second imaging mode or earlier than the time of reading charges in the second mode.

Further, as an example, it is presumed that an X-ray imaging apparatus includes the X-ray generation unit 104 for radiating the X-ray to a subject, the X-ray detection unit 105 having a plurality of detection elements for detecting the X-ray penetrating the subject and storing charges, the X-ray image generation unit for sequentially reading the charges stored in the detection elements to generate an X-ray image, and the transfer unit for transferring the X-ray image generated by the X-ray image generation unit to an apparatus control unit, wherein the apparatus control unit includes a display unit for displaying the received X-ray image.

The X-ray imaging apparatus further includes the imaging unit for the first imaging mode and the second imaging mode, the imaging mode switching unit 103 for switching from the first imaging mode to the second imaging mode, and an imaging mode changeover generation detection unit 110 for detecting processing of the first imaging mode during which an imaging mode changeover occurs. The X-ray imaging apparatus further includes the imaging mode end processing unit 111 for switching processing for ending the first imaging mode according to the processing detected by the X-ray generation unit 104.

The first imaging mode is any one of pulsed X-ray radioscopic imaging, continuous X-ray radioscopic imaging, pulsed serial imaging, and continuous serial imaging. The second imaging mode is any one of general imaging, pulsed serial imaging, and continuous serial imaging. The imaging mode switching unit 103 determines, when a mode changeover request is generated in the first imaging mode, that an imaging mode changeover from the first imaging mode to the second imaging mode has occurred.

The imaging mode changeover generation detection unit 110 classifies the processing of the first imaging mode into data read processing, charge storage processing, and image transfer processing, and determines processing of the first imaging mode in which an imaging mode changeover has occurred. When both the charge storage processing and the X-ray radiation processing have occurred when an imaging mode changeover has occurred, the imaging mode changeover generation detection unit 110 determines that an imaging mode changeover has occurred in the charge storage processing of the first imaging mode.

When both the charge storage processing and the image transfer processing have occurred when an imaging mode changeover has occurred, the imaging mode changeover generation detection unit 110 determines that an imaging mode changeover has occurred in the image transfer processing of the first imaging mode.

When both the charge read processing and the image transfer processing have occurred when an imaging mode changeover has occurred, the imaging mode changeover generation detection unit 110 determines that an imaging mode changeover has occurred in the image transfer processing of the first imaging mode.

When the imaging mode changeover generation detection unit 110 detects an imaging mode changeover during the data read processing, the imaging mode end processing unit 111 performs wait processing for a time Tp calculated by Tp=b*(Tt−Ta) (0.0≤b) after the data read processing and then ends the first imaging mode, where Ta indicates an image read time during X-ray radioscopic imaging, and Tt indicates an image transfer time during X-ray radioscopic imaging.

When the imaging mode changeover generation detection unit 110 detects an imaging mode changeover during the charge storage processing, the imaging mode end processing unit 111 performs wait processing for a time Tp calculated by Tp=b*Tt (0.0≤b) after the data read processing and then ends the first imaging mode, where Tt is an image transfer time during X-ray radioscopic imaging.

When the imaging mode changeover generation detection unit 110 detects an imaging mode changeover during the image transfer processing, the imaging mode end processing unit 111 ends the first imaging mode after completion of the image transfer processing. During the preparation processing for switching from the first imaging mode to the second imaging mode, the imaging mode switching unit 103 performs at least once the processing for erasing an image lag in the X-ray detection unit 105 which occurs in the first imaging mode.

The imaging mode switching unit 103 performs the processing for erasing an image lag at the same time as the time of reading charges in the second imaging mode or earlier than the time of reading charges in the second mode. When switching from the first imaging mode to the second imaging mode, the imaging mode switching unit 103 performs wait processing for a predetermined time Tw.

Although an X-ray imaging apparatus has been described in the above-described exemplary embodiments, the present invention is applicable to control of an imaging system for visible light and non-X-ray radiation which executes a plurality of imaging modes for detecting light or radiation to acquire an image. In this case, the X-ray generation unit 104 is replaced by the radiation generation unit, and the X-ray detection unit 105 is replaced by the radiation detection unit. In the case of an imaging system using electromagnetic waves affecting the human body, such as the X-ray and radiation, the ability to grasp the timing of imaging enables reducing mis-imaging and re-imaging, thus reducing unnecessary exposure of the subject.

Although, in the first to third exemplary embodiments, the first imaging mode end measurement unit 108 of the imaging control unit 107 performs timing measurement, an exemplary embodiment is not limited thereto. If the X-ray detection unit 105 is provided with the function of the first imaging mode end measurement unit 108 and performs timing measurement within the X-ray detection unit 105, the influence of communication delay can be reduced. Further, if the X-ray detection unit 105 determines the delay time Tf in the fourth to sixth exemplary embodiments and the wait time Twin the first to sixth exemplary embodiments, the influence of communication delay can be reduced.

Although, in the fourth to sixth exemplary embodiments, the X-ray detection unit 105 detects the system state, the X-ray detection unit 105 may acquire and detect the state of the X-ray generation unit 104.

The embodiment of the present invention also includes the following processing. Specifically, software (programs) for achieving the functions of the exemplary embodiments described with reference to FIGS. 2, 9, 15, and 22 is supplied to a system or apparatus via a network or various storage media. A computer (or a central processing unit (CPU) or a microprocessor unit (MPU)) of the system or apparatus reads and executes the programs.

Other Embodiments embodiments of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the embodiment of the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-288682 filed Dec. 28, 2011, which is hereby incorporated by reference herein in its entirety.

What is claimed is:

1. An imaging control apparatus for executing initialization operation for repetitively reading an electrical signal from a sensor, the imaging control apparatus comprising:
a detection unit configured to detect an instruction for starting an imaging mode;
an acquisition unit configured to acquire an imaging mode related to the instruction and a sensor state when the instruction is generated; and
a control unit configured to, based on the acquired imaging mode and sensor state, perform control so that the reading repetition interval in the initialization operation at the time of transition from a predetermined imaging mode to the still image capturing mode is shorter than the interval in the initialization operation at the time of transition from a non-imaging state to the still image capturing mode.

2. The imaging control unit according to claim 1, wherein the control unit performs control so that in the initialization operation at the time of transition from a predetermined imaging mode to the still image capturing mode, the reading repetition interval is shorter and the number of repetitions is greater than those in the initialization operation at the time of transition from a non-imaging state to the still image capturing mode.

3. The imaging control unit according to claim 1, wherein, at the time of transition from the predetermined imaging mode to the still image capturing mode, the control unit waits for at least a specific wait time after the instruction is generated, and then performs control for executing the initialization operation.

4. The imaging control unit according to claim 3, further comprising:
a selection unit configured to select whether the control unit waits based on setting information.

5. The imaging control unit according to claim 3, wherein the predetermined imaging mode is a moving image capturing mode, and
wherein the control unit changes the wait time according to the frame rate in the moving image capturing mode.

6. The imaging control unit according to claim 3, wherein the control unit waits for at least a specific wait time after completing the predetermined imaging mode and before the initialization operation at the time of transition to the still image capturing mode, and then performs control for executing the initialization operation.

7. The imaging control unit according to claim 6, further comprising:
a determination unit configured to determine the specific wait time according to a time duration since the instruction is given until the predetermined imaging mode ends.

8. The imaging control unit according to claim 1, further comprising:
a selection unit configured to select, according to setting information, that the initialization operation is performed after interrupting, when the instruction is given, one unit of imaging processing in the predetermined imaging mode according to the instruction, or that the initialization operation is performed after completion of the one unit of imaging processing.

9. A radiographic imaging system comprising:
the imaging control apparatus according to claim 1;
a radiation generation unit; and
the sensor configured to detect radiation generated by the radiation generation unit.

* * * * *